US009696328B2

(12) United States Patent
Hansen et al.

(10) Patent No.: US 9,696,328 B2
(45) Date of Patent: Jul. 4, 2017

(54) AUTOMATED SYSTEM FOR ISOLATING, AMPLIFYING AND DETECTING A TARGET NUCLEIC ACID SEQUENCE

(75) Inventors: Timothy R. Hansen, Spring Grove, PA (US); Matthew P. Collis, Seven Valleys, PA (US); Bradley S. Thomas, Timonium, MD (US); Thomas L. Fort, Hanover, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 266 days.

(21) Appl. No.: 13/551,830

(22) Filed: Jul. 18, 2012

(65) Prior Publication Data

US 2012/0282603 A1 Nov. 8, 2012

Related U.S. Application Data

(63) Continuation of application No. 13/094,140, filed on Apr. 26, 2011, now abandoned, which is a
(Continued)

(51) Int. Cl.
*B01L 3/00* (2006.01)
*C12M 1/00* (2006.01)
(Continued)

(52) U.S. Cl.
CPC ...... *G01N 35/0099* (2013.01); *B01L 3/50855* (2013.01); *B01L 2300/0829* (2013.01); *G01N 35/0098* (2013.01); *G01N 35/026* (2013.01); *G01N 35/028* (2013.01); *G01N 35/1065* (2013.01); *G01N 35/1074* (2013.01);
(Continued)

(58) Field of Classification Search
CPC ......... G01N 2035/1025; G01N 35/028; G01N 35/0099; B01L 2300/0829; B01L 3/50855; C12M 47/10; C12M 47/02
See application file for complete search history.

(56) References Cited

U.S. PATENT DOCUMENTS 3,533,744 A 10/1970 Unger
3,627,431 A 12/1971 Komarniski
(Continued)

FOREIGN PATENT DOCUMENTS

EP 0508531 A2 10/1992
EP 0640828 A1 3/1995
(Continued)

OTHER PUBLICATIONS

Bactec ® 9120/9240 Brochure, Becton Dickinson and Company, 1993.
(Continued)

*Primary Examiner* — Nathan Bowers
(74) *Attorney, Agent, or Firm* — Botos Churchill IP Law LLP

(57) ABSTRACT

A system and method for preparing and testing of targeted nucleic acids is presented. The system integrates a pipetter, extractor, assay reader, and other components, including a selectively compliant articulated robot arm (SCARA). This synergistic integration of previously separate diagnostic tools creates a system and method whereby a minimum of human intervention is required. The resulting system provides a substantially more accurate and precise method of isolating, amplifying and detecting targeted nucleic acids for diagnosing diseases.

14 Claims, 21 Drawing Sheets

Related U.S. Application Data continuation of application No. 12/379,053, filed on Feb. 11, 2009, now abandoned, which is a continuation of application No. 10/440,422, filed on May 19, 2003, now abandoned.

(60) Provisional application No. 60/380,859, filed on May 17, 2002.

(51) Int. Cl.
*G01N 35/00* (2006.01)
*G01N 35/02* (2006.01)
*G01N 35/10* (2006.01)
*G01N 35/04* (2006.01)

(52) U.S. Cl.
CPC .............. *G01N 2035/00366* (2013.01); *G01N 2035/0405* (2013.01); *G01N 2035/1025* (2013.01); *G01N 2035/1053* (2013.01); *Y10T 436/143333* (2015.01)

(56) References Cited

U.S. PATENT DOCUMENTS

| | | |
|---|---|---|
| 3,773,426 A | 11/1973 | Mudd |
| 3,792,276 A | 2/1974 | Toman et al. |
| 3,844,428 A | 10/1974 | Olsen |
| 3,852,599 A | 12/1974 | Smith |
| 3,857,485 A | 12/1974 | Frank |
| 3,883,742 A | 5/1975 | Olson et al. |
| 3,885,879 A | 5/1975 | Louder et al. |
| 3,890,505 A | 6/1975 | Olson |
| 3,898,457 A | 8/1975 | Packard et al. |
| 3,899,673 A | 8/1975 | Packard |
| 3,924,128 A | 12/1975 | Frank |
| 3,926,323 A | 12/1975 | Frank et al. |
| 3,972,778 A | 8/1976 | Cunningham |
| 3,988,240 A | 10/1976 | Fraas |
| 4,002,909 A | 1/1977 | Packard et al. |
| 4,004,150 A | 1/1977 | Natelson |
| 4,101,174 A | 7/1978 | Miller |
| 4,115,010 A | 9/1978 | McAleer et al. |
| 4,147,250 A | 4/1979 | Schulz |
| 4,201,478 A | 5/1980 | Gerlier et al. |
| 4,240,751 A | 12/1980 | Linnecke et al. |
| 4,259,290 A | 3/1981 | Suovaniemi et al. |
| 4,340,390 A | 7/1982 | Collins et al. |
| 4,343,991 A | 8/1982 | Fujiwara et al. |
| 4,349,510 A | 9/1982 | Kolehmainen et al. |
| 4,358,203 A | 11/1982 | Citrin |
| 4,431,307 A | 2/1984 | Suovaniemi |
| 4,438,068 A | 3/1984 | Forrest |
| 4,465,938 A | 8/1984 | Kato et al. |
| 4,472,352 A | 9/1984 | Quesneau et al. |
| 4,483,825 A | 11/1984 | Fatches |
| 4,486,539 A | 12/1984 | Ranki et al. |
| 4,498,780 A | 2/1985 | Banno et al. |
| 4,498,782 A | 2/1985 | Proctor et al. |
| 4,557,726 A | 12/1985 | Reinicke |
| 4,651,006 A | 3/1987 | Valenta |
| 4,672,200 A | 6/1987 | Claypool et al. |
| 4,683,195 A | 7/1987 | Mullis et al. |
| 4,683,202 A | 7/1987 | Mullis |
| 4,722,606 A | 2/1988 | Bonfiglio et al. |
| 4,727,033 A | 2/1988 | Hijikata et al. |
| 4,730,921 A | 3/1988 | Klein et al. |
| 4,737,464 A | 4/1988 | McConnell et al. |
| 4,751,177 A | 6/1988 | Stabinsky |
| 4,762,105 A | 8/1988 | Beyer et al. |
| 4,762,420 A | 8/1988 | Bowley |
| 4,772,453 A | 9/1988 | Lisenbee |
| 4,778,451 A | 10/1988 | Kamen |
| 4,778,763 A | 10/1988 | Makiguchi et al. |
| 4,780,833 A | 10/1988 | Atake |
| 4,794,085 A | 12/1988 | Jessop et al. |
| 4,800,159 A | 1/1989 | Mullis et al. |
| 4,800,750 A | 1/1989 | Enhorning |
| 4,844,887 A | 7/1989 | Galle et al. |
| 4,846,003 A | 7/1989 | Marquiss |
| 4,864,856 A | 9/1989 | Ichikawa et al. |
| 4,892,409 A | 1/1990 | Smith |
| 4,893,515 A | 1/1990 | Uchida |
| 4,895,650 A | 1/1990 | Wang |
| 4,896,963 A | 1/1990 | Kato |
| 4,929,828 A | 5/1990 | Claypool |
| 4,936,687 A | 6/1990 | Lilja et al. |
| 4,940,332 A | 7/1990 | Miwa et al. |
| 4,946,958 A | 8/1990 | Campbell et al. |
| 4,950,613 A | 8/1990 | Arnold, Jr. et al. |
| 4,968,148 A | 11/1990 | Chow et al. |
| 5,013,529 A | 5/1991 | Itoh |
| 5,036,001 A | 7/1991 | Gork et al. |
| 5,073,029 A | 12/1991 | Eberly et al. |
| 5,075,077 A | 12/1991 | Durley, III et al. |
| 5,112,134 A | 5/1992 | Chow et al. |
| 5,124,041 A | 6/1992 | Sheer et al. |
| 5,126,276 A | 6/1992 | Fish et al. |
| 5,133,392 A | 7/1992 | Hamann et al. |
| 5,139,745 A | 8/1992 | Barr et al. |
| 5,144,136 A | 9/1992 | Kubisiak |
| 5,146,093 A | 9/1992 | Valenta et al. |
| 5,169,601 A | 12/1992 | Ohta et al. |
| 5,173,741 A | 12/1992 | Wakatake |
| 5,192,692 A | 3/1993 | Sakai et al. |
| 5,195,282 A | 3/1993 | Campbell |
| 5,198,670 A | 3/1993 | VanCauter et al. |
| 5,202,091 A | 4/1993 | Lisenbee |
| 5,216,488 A | 6/1993 | Tguunanen et al. |
| 5,234,665 A | 8/1993 | Ohta et al. |
| 5,252,296 A | 10/1993 | Zuckermann et al. |
| 5,270,210 A | 12/1993 | Weyrauch et al. |
| 5,281,394 A | 1/1994 | Holub |
| 5,281,540 A | 1/1994 | Merkh et al. |
| 5,298,753 A | 3/1994 | Sonne et al. |
| 5,304,492 A | 4/1994 | Klinkhammer |
| 5,307,144 A | 4/1994 | Hiroshi et al. |
| 5,314,825 A | 5/1994 | Weyrauch et al. |
| 5,319,436 A | 6/1994 | Manns et al. |
| 5,320,808 A | 6/1994 | Holen et al. |
| 5,324,635 A | 6/1994 | Kawase et al. |
| 5,325,295 A | 6/1994 | Fratantoni et al. |
| 5,330,916 A | 7/1994 | Williams et al. |
| 5,333,675 A | 8/1994 | Mullis et al. |
| 5,376,313 A | 12/1994 | Kanewske, III et al. |
| 5,399,491 A | 3/1995 | Kacian et al. |
| 5,407,638 A | 4/1995 | Wang |
| 5,427,930 A | 6/1995 | Birkenmeyer et al. |
| 5,437,990 A | 8/1995 | Burg et al. |
| 5,443,791 A | 8/1995 | Cathcart et al. |
| 5,445,794 A | 8/1995 | Wihlborg |
| 5,447,687 A | 9/1995 | Lewis et al. |
| 5,455,008 A | 10/1995 | Earley et al. |
| 5,457,527 A | 10/1995 | Manns et al. |
| 5,463,895 A | 11/1995 | Brentz |
| 5,468,453 A | 11/1995 | Holt et al. |
| 5,473,437 A | 12/1995 | Blumenfeld et al. |
| 5,482,861 A | 1/1996 | Clark et al. |
| 5,483,347 A | 1/1996 | Hollmann |
| 5,488,854 A | 2/1996 | Kawanabe et al. |
| 5,490,971 A | 2/1996 | Gifford et al. |
| 5,496,523 A | 3/1996 | Gazit et al. |
| 5,499,545 A | 3/1996 | Kimura et al. |
| 5,500,188 A | 3/1996 | Hafeman et al. |
| 5,503,036 A | 4/1996 | Nguyen et al. |
| 5,508,200 A | 4/1996 | Tiffany et al. |
| 5,516,490 A | 5/1996 | Sanadi |
| 5,518,923 A | 5/1996 | Berndt et al. |
| 5,537,880 A | 7/1996 | Takeda et al. |
| 5,538,849 A | 7/1996 | Uematsu et al. |
| 5,540,081 A | 7/1996 | Takeda et al. |
| 5,550,025 A | 8/1996 | Walker |
| 5,554,516 A | 9/1996 | Kacian et al. |
| 5,567,326 A | 10/1996 | Ekenberg et al. |
| 5,578,270 A | 11/1996 | Reichler et al. |

(56) References Cited

U.S. PATENT DOCUMENTS

| | | |
|---|---|---|
| 5,593,867 A | 1/1997 | Walker et al. |
| 5,604,101 A | 2/1997 | Hanley et al. |
| 5,604,130 A | 2/1997 | Warner et al. |
| 5,612,227 A | 3/1997 | Inoue et al. |
| 5,622,869 A | 4/1997 | Lewis et al. |
| 5,656,493 A | 8/1997 | Mullis et al. |
| 5,681,478 A | 10/1997 | Lea et al. |
| 5,684,712 A | 11/1997 | Goffe et al. |
| 5,686,271 A | 11/1997 | Mian et al. |
| 5,686,272 A | 11/1997 | Marshall et al. |
| 5,714,127 A | 2/1998 | DeWitt et al. |
| 5,714,380 A | 2/1998 | Neri et al. |
| 5,723,795 A | 3/1998 | Merriam |
| 5,750,338 A | 5/1998 | Collins et al. |
| 5,750,881 A | 5/1998 | Dorenkott et al. |
| 5,780,224 A | 7/1998 | Collins |
| 5,804,067 A | 9/1998 | McDonald et al. |
| 5,814,275 A | 9/1998 | Lewis et al. |
| 5,834,197 A | 11/1998 | Parton |
| 5,851,491 A | 12/1998 | Moulton |
| 5,853,665 A | 12/1998 | Ade et al. |
| 5,882,903 A | 3/1999 | Andrevski et al. |
| 5,895,631 A | 4/1999 | Tajima |
| 5,915,282 A | 6/1999 | Merriam et al. |
| 5,918,291 A | 6/1999 | Inacu et al. |
| 5,965,828 A | 10/1999 | Merriam |
| 5,973,138 A | 10/1999 | Collis |
| 6,008,055 A | 12/1999 | Zhu et al. |
| 6,022,747 A | 2/2000 | Gherson et al. |
| 6,033,574 A | 3/2000 | Siddiqi |
| 6,043,880 A | 3/2000 | Andrews et al. |
| 6,060,320 A | 5/2000 | Dorenkott et al. |
| 6,079,283 A | 6/2000 | Papen et al. |
| 6,094,966 A | 8/2000 | Papen et al. |
| 6,100,079 A | 8/2000 | Tajima |
| 6,121,049 A | 9/2000 | Dorenkott et al. |
| 6,216,049 B1 | 4/2001 | Yang et al. |
| 6,267,927 B1 | 7/2001 | Pomar Longedo et al. |
| 6,296,702 B1 | 10/2001 | Bryning et al. |
| 6,335,166 B1 | 1/2002 | Ammann et al. |
| 6,350,570 B1 | 2/2002 | Bienert et al. |
| 6,368,561 B1 | 4/2002 | Rutishauser et al. |
| 6,413,780 B1 | 7/2002 | Bach et al. |
| 6,572,458 B2 | 6/2003 | Lim |
| 6,890,742 B2 | 5/2005 | Ammann et al. |
| 7,118,892 B2 | 10/2006 | Ammann et al. |
| 7,482,143 B2 | 1/2009 | Ammann et al. |
| 7,524,652 B2 | 4/2009 | Ammann et al. |
| 7,560,255 B2 | 7/2009 | Ammann et al. |
| 2002/0014443 A1 | 2/2002 | Hansen et al. |
| 2002/0041829 A1 | 4/2002 | Kowallis |
| 2002/0068821 A1 | 6/2002 | Gundling |
| 2002/0094578 A1 | 7/2002 | Kowallis et al. |
| 2004/0149015 A1 | 8/2004 | Hansen et al. |
| 2004/0157219 A1 | 8/2004 | Lou et al. |

FOREIGN PATENT DOCUMENTS

| | | |
|---|---|---|
| EP | 0753750 A2 | 1/1997 |
| EP | 0810438 A2 | 12/1997 |
| EP | 0905520 A1 | 3/1999 |
| JP | 56164958 A | 12/1981 |
| JP | 60206028 A | 10/1985 |
| JP | 63029251 A | 2/1988 |
| JP | 63029253 A | 2/1988 |
| JP | 8266267 A | 10/1996 |
| JP | 2001149097 A | 6/2001 |
| JP | 2001169771 A | 6/2001 |
| JP | 2002098704 A | 4/2002 |
| WO | 8801302 A1 | 2/1988 |
| WO | 8810313 A1 | 12/1988 |
| WO | 8810315 A1 | 12/1988 |
| WO | 9112079 A1 | 8/1991 |
| WO | 9208545 A1 | 5/1992 |
| WO | 9530139 A1 | 11/1995 |
| WO | 9609550 A1 | 3/1996 |
| WO | 9716561 A1 | 5/1997 |
| WO | 0033087 A1 | 6/2000 |
| WO | 0043534 A1 | 7/2000 |
| WO | 0072969 A1 | 12/2000 |
| WO | 0110554 A2 | 2/2001 |
| WO | 0131317 A1 | 5/2001 |
| WO | 0189705 A2 | 11/2001 |

OTHER PUBLICATIONS

Bactec ® 9240 Brochure, Becton Dickinson and Company, 1993.
CytoFluor II Multi-Well Fluorescence Plate Readers, PerSeptive BioSystems, 1996.
English Translation Tamatsukuri, S., Development of Diagnostic Technology Using Magnetic Microparticles,of: Bio Industry, 21(8):39-47.
FLUOstar Microplate Fluorometer, BMG Lab Technologies GmbH, Oct. 1995.
Fmax Fluorescence Microplate System, Molecular Devices, 1996.
Nickerson, D., et al., Automated DNA Diagnostics Using an ELISA-Based Oligonucleotide, Proc. Natl. Acad. Sci. USA, 87:8923-8927 (1990).
Obata, K., et al., Development of a Novel Method for Operating Magnetic Particles, Magtration Technology, and Its Use forAutomating Nucleic Acid Purification, Journal of Bioscience and Bioengineering, 91(5):500-503 (2001).
Office Action from Corresponding Japanese Application 2004-506467, mailed Jan. 8, 2010.
SPECTRAmax 340 Tunable Microplate Reader, Molecular Devices, 1997.

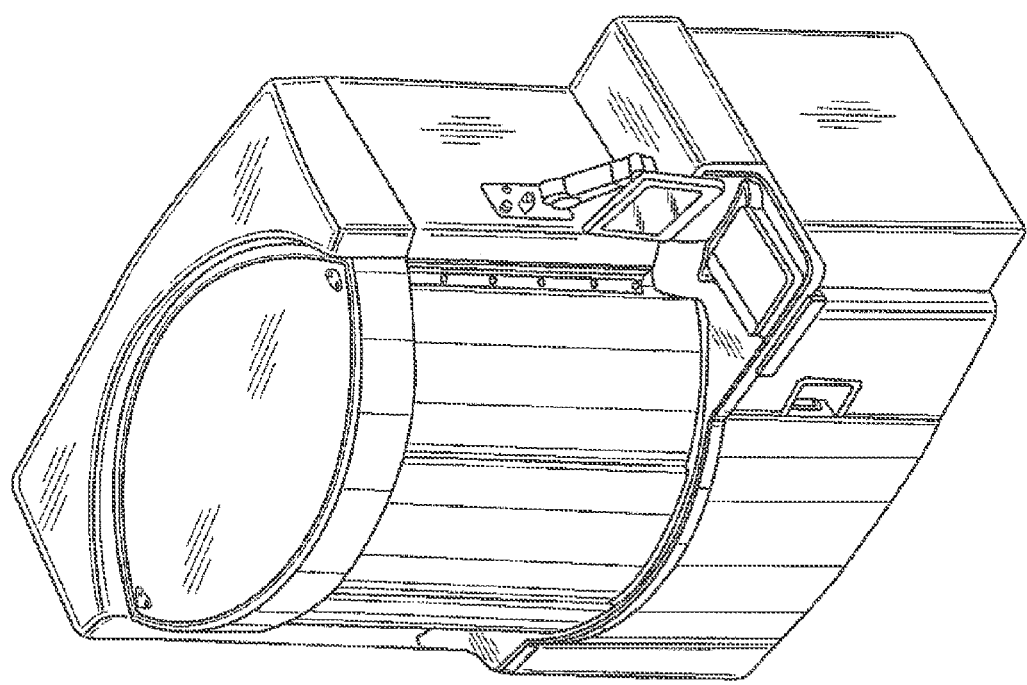
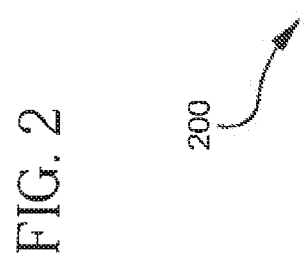
FIG. 2

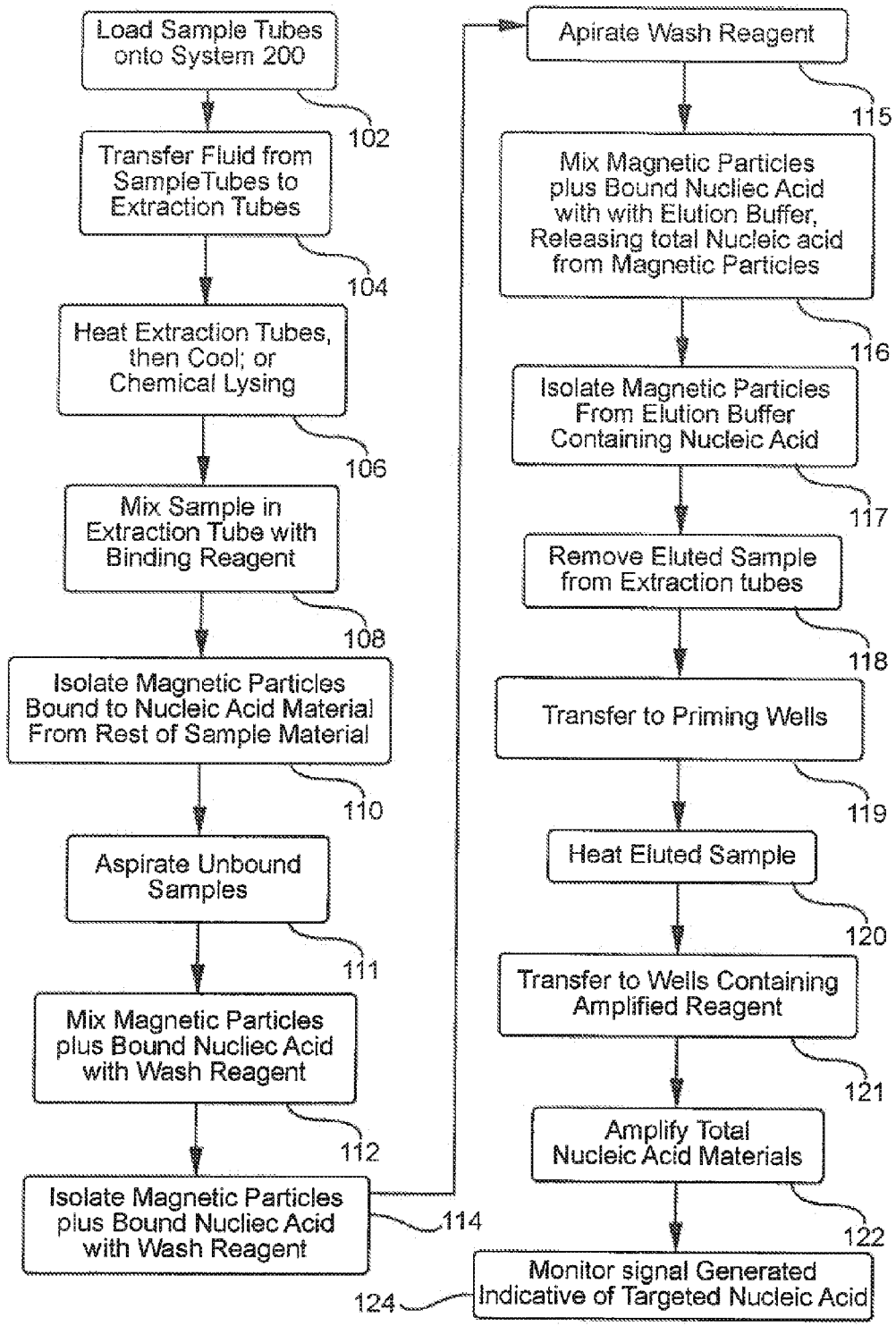

AUTOMATED SYSTEM FOR ISOLATING, AMPLIFYING AND DETECTING A TARGET NUCLEIC ACID SEQUENCE

CROSS-REFERENCE TO RELATED APPLICATIONS

This application is a continuation of U.S. application Ser. No. 13/094,140, filed on Apr. 26, 2011, which is a continuation of U.S. application Ser. No. 12/379,053, filed on Feb. 11, 2009, which is a continuation of U.S. application Ser. No. 10/440,422, filed on May 19, 2003, which claims the benefit of Application Ser. No. 60/380,859, filed on May 17, 2002, the disclosures of which are hereby incorporated herein by reference.

FIELD OF THE INVENTION

The invention is related to the detection of nucleic acids. More particularly, the invention is related to a system and method for the isolation, amplification and detection of targeted nucleic acids in a fully automated and integrated system that comprises a pipetter, extractor and an assay reader, as well as many other devices, to detect the targeted nucleic acids. Related subject matter is disclosed in co-pending U.S. provisional patent application Ser. No. 60/380,859, filed May 17, 2002, the entire contents of which are incorporated by reference. Related subject matter is disclosed in co-pending U.S. provisional patent application Ser. No. 60/380,859, filed May 17, 2002, the entire contents of which are incorporated by reference.

BACKGROUND OF THE INVENTION

None of the references described or referred to herein are admitted to be prior art to the claimed invention.

A variety of molecular biology methodologies, such as nucleic acid sequencing, direct detection of particular nucleic acids sequences by nucleic acid hybridization, and nucleic acid sequence amplification techniques, require that the nucleic acids (DNA or RNA) be separated from the remaining cellular components. This process generally includes the steps of collecting the cells in a sample tube and lysing the cells with heat and/or reagent(s) which causes the cells to burst and release the nucleic acids (DNA or RNA) into the solution in the tube. The tube is then placed in a centrifuge, and the sample is spun down so that the various components of the cells are separated into density layers within the tube. The layer of the nucleic acids can be removed from the sample by a pipette or any suitable instrument. The samples can then be washed and treated with appropriate reagents, such as fluorescein probes, so that the nucleic acids can be detected in an apparatus such as the BDProbeTec® ET system, manufactured by Becton Dickinson and Company and described in U.S. Pat. No. 6,043,880 to Andrews et al., the entire contents of which is incorporated herein by reference.

Although the existing techniques for separating nucleic acids from cell samples may be generally suitable, such methods are typically time consuming and complex. When performed manually, the complexity and number of processing steps associated with a nucleic acid based assay also introduce opportunities for practitioner error, exposure to pathogens and cross contamination between assays. Furthermore, although the centrifuging process is generally effective in separating the nucleic acids from the other cell components, certain impurities having the same or similar density as the nucleic acids can also be collected in the nucleic acid layer, and must be removed from the cell sample with the nucleic acids.

A technique has recently been developed which is capable of more effectively separating nucleic acids from the remaining components of cells. This technique involves the use of paramagnetic particles, and is described in U.S. Pat. No. 5,973,138 to Mathew P. Collis, the entire contents of which is incorporated herein by reference.

In this technique, paramagnetic or otherwise magnetic or magnetizable particles are placed in an acidic solution along with cell samples. When the cell samples are lysed to release the nucleic acids, the nucleic acids are reversibly bound to the particles. The particles can then be separated from the remainder of the solution by known techniques such as centrifugation, filtering or magnetic force. The particle to which the nucleic acids are bound can then be removed from the solution and placed in an appropriate buffer solution, which causes the nucleic acids to become unbound from the particles. The particles can then be separated from the nucleic acids by any of the techniques described above.

Examples of systems and method for manipulating magnetic particles are described in U.S. Pat. Nos. 3,988,240, 4,895,650, 4,936,687, 5,681,478, 5,804,067 and 5,567,326, in European Patent Application No. EP905520A1, and in published PCT Application WO 96/09550, the entire contents of each of said documents being incorporated herein by reference.

Techniques also exist for moving solutions between containers, such as test tubes, sample wells, and so on. In an automated pipetting technique, in order to properly control a pipetter device to draw fluid from a sample container such as a test tube, it is necessary to know the level of the sample fluid in the tube so the pipette can be lowered to the appropriate depth. It is also necessary to detect whether the pipette tip has been properly connected to the pipetter device. Prior methods to detect the level of a fluid in a container include the use of electrical conductivity detection. This method requires the use of electrically conductive pipette tips connected to a sensitive amplifier which detects small changes in the electrical capacitance of the pipette tip when it comes in contact with an ionic fluid. Pipette tip detection in this known system is achieved by touching the end of the conductive pipette tip to a grounded conductor. Drawbacks of this approach include the higher cost of conductive pipette tips, and that the method only works effectively with ionic fluids. In other words, if the fluid is non-conductive, it will not provide a suitable electrical path to complete the circuit between the conductors in the pipette tip.

A system and method for the measurement of the level of fluid in a pipette tube has been described in U.S. Pat. No. 4,780,833, issued to Atake, the contents of which are herein incorporated by reference. Atake's system and method involves applying suction to the liquid to be measured, maintaining liquid in a micro-pipette tube or tubes, and providing the tubes with a storage portion having a large inner diameter and a slender tubular portion with a smaller diameter. A pressure gauge is included for measuring potential head in the tube or tubes. Knowing the measured hydraulic head in the pipette tube and the specific gravity of the liquid, the amount of fluid contained in the pipette tube can be ascertained.

Devices used in molecular biology methodologies can incorporate the pipette device mentioned above, with robotics, to provide precisely controlled movements to safely and carefully move sample biological fluids from one container to another. Typically, these robotic devices are capable of coupling to one or more of the aforementioned pipette tips, and employ an air pump or other suitable pressurization device to draw the sample biological fluid into the pipette tips.

The advent of DNA probes, which can identify a specific bacteria by testing for the presence of a unique bacterial DNA sequence in the sample obtained from the patient, has greatly increased the speed and reliability of clinical diagnostic testing. A test for the tuberculosis mycobacterium, for example, can be completed within a matter of hours using DNA probe technology. This allows treatment to begin more quickly and avoids the need for long patient isolation times. The nucleic acid sequence separating technique and the pipetting technique described above can be used to prepare samples to be used in conjunction with DNA probe technology for diagnostic purposes.

In the use of DNA probes for clinical diagnostic purposes, a nucleic acid amplification reaction is usually carried out in order to multiply the target nucleic acid into many copies or amplicons. Examples of nucleic acid amplification reactions include strand displacement amplification (SDA), rolling circle amplification (RCA), self-sustained sequence replication (3SR), transcription-mediated amplification (TMA), nucleic acid-sequence-based amplification (NASBA), ligase chain reaction (LCR) and polymerase chain reaction (PCR). Methods of nucleic acid amplification are described in the literature. For example, PCR amplification, for instance, is described by Mullis et al. in U.S. Pat. Nos. 4,683,195, 4,683,202 and 4,800,159, and in Methods in Enzymology, 155:335-350 (1987). Examples of SDA can be found in Walker, PCR Methods and Applications, 3:25-30 (1993), Walker et al. in Nucleic Acids Res., 20:1691-1996 (1992) and Proc. Natl. Acad. Sci., 89:392-396 (1991). LCR is described in U.S. Pat. Nos. 5,427,930 and 5,686,272. And different TAA formats are provided in publications such as Burg et al. in U.S. Pat. No. 5,437,990; Kacian et al. in U.S. Pat. Nos. 5,399,491 and 5,554,516; and Gingeras et al. in International Application No. PCT/US87/01966 and International Publication No. WO 88/01302, and International Application No. PCT/US88/02108 and International Publication No. WO 88/10315.

Detection of the nucleic acid amplicons can be carried out in several ways, all involving hybridization (binding) between the target DNA and specific probes. Many common DNA probe detection methods involve the use of fluorescein dyes. One detection method is fluorescence energy transfer. In this method, a detector probe is labeled both with a fluorescein dye that emits light when excited by an outside source, and with a quencher which suppresses the emission of light from the fluorescein dye in its native state. When DNA amplicons are present, the fluorescein-labeled probe binds to the amplicons, is extended, and allows fluorescence emission to occur. The increase of fluorescence is taken as an indication that the disease-causing bacterium is present in the patient sample.

Other detection methods will be apparent to those skilled in the art. For example, a single fluorescent label may be employed on the reporter moiety with detection of a change in fluorescence polarization in the presence of the complement of the reporter moiety (see U.S. Pat. No. 5,593,867). Non-fluorescent labels are also useful. For example, the reporter moiety may be labeled with a lipophilic dye and contain a restriction site which is cleaved in the presence of the complement of the reporter moiety (see U.S. Pat. No. 5,550,025). Alternatively, the reporter probe may be radiolabeled and the products resulting from synthesis of the complement of the reporter moiety may be resolved by electrophoresis and visualized by autoradiography. Immunological labels may also be employed. A reporter probe labeled with a hapten can be detected after synthesis of the complement of the reporter moiety by first removing unreacted reporter probe (for example by adapter-specific capture on a solid phase) and then detecting the hapten label on the reacted reporter probe using standard chemiluminescent or colorimetric ELISAs. A biotin label may be substituted for the hapten and detected using methods known in the art. Chemiluminescent compounds which include acridiuium esters which can be used in a hybridization protection assay (HPA) and then detected with a luminometer (see U.S. Pat. Nos. 4,950,613 and 4,946,958).

One broad category of detection devices that can be used in the various embodiments of the invention (more fully described in detail below), are optical readers and scanners. Several types of optical readers or scanners exist which are capable of exciting fluid samples with light, and then detecting any light that is generated by the fluid samples in response to the excitation. For example, an X-Y plate scanning apparatus, such as the CytoFluor Series 4000 made by PerSeptive Biosystems, is capable of scanning a plurality of fluid samples stored in an array or plate of microwells. The apparatus includes a scanning head for emitting light toward a particular sample, and for detecting light generated from that sample. The apparatus includes first and second optical cables each having first and second ends. The first ends of the optical cables are integrated to form a single Y-shaped "bifurcated" cable. The scanning head includes this end of the bifurcated optical cable. The second end of the first optical cable of the bifurcated cable is configured to receive light from a light emitting device, such as a lamp, and the second end of the second cable of the bifurcated cable is configured to transmit light to a detector, such as a photomultiplier tube.

During operation, the optical head is positioned so that the integrated end of the bifurcated optical fiber is at a suitable position with respect to one of the microwells. The light emitting device is activated to transmit light through the first optical cable of the bifurcated optical cable such that the light is emitted out of the integrated end of the bifurcated optical cable toward the sample well. If fluid sample fluoresces in response to the emitted light, the light produced by the fluorescence is received by the integrated end of the optical fiber and is transmitted through the second optical fiber to the optical detector. The detected light is converted by the optical detector into an electrical signal, the magnitude of which is indicative of the intensity of the detected light. The electrical signal is processed by a computer to determine whether the target DNA is present or absent in the fluid sample based on the magnitude of the electrical signal.

Another existing type of apparatus is described in U.S. Pat. No. 5,473,437, to Blumenfeld et al. This apparatus includes a tray having openings for receiving bottles of fluid samples. The tray includes a plurality of optical fibers which each have an end that terminates at a respective opening in the tray. The tray is connected to a wheel, and rotates in conjunction with the rotation of the wheel. The other ends of the optical fibers are disposed circumferentially in succession about the wheel, and a light emitting device is configured to emit light toward the wheel so that as the wheel rotates, the ends of the optical fibers sequentially receive the light being emitted by the light emitting device. That is, when the wheel rotates to a first position, a fiber extending from the wheel to one of the openings becomes aligned with the optical axis of the light emitting device and thus, the emitted light will enter that fiber and be transmitted to the opening. The apparatus further include a light detector having an optical axis aligned with the optical axis of the emitted light. Accordingly, if the sample in the bottle housed in the opening fluoresces due to the excitation light, the light emitted from the sample will transmit through the optical fiber and be detected by the detector. The wheel then continues to rotate to positions where the ends of the other optical fibers become aligned with the optical axis of the light emitter and light detector, and the light emission and detection process is repeated to sample the fluid samples in the bottles housed in the openings associated with those fibers.

Another type of optical testing apparatus is described in U.S. Pat. No. 5,518,923, to Berndt et al. That apparatus includes a plurality of light emitter/light detector devices for testing a plurality of fluid samples. The fluid samples are contained in jars which are placed in the openings of a disk-shaped tray. The plurality of the light emitter/detector devices is disposed in the radial direction of the tray. Hence, as the tray rotates, the samples in each circular row will pass by their respective light emitter/detector device, which will transmit light into the sample and detect any light that is generated by the sample in response to the emitted light. In theory, this apparatus is capable of testing more than one sample at any given time. However, in order to achieve this multiple sample testing ability, the system must employ a plurality of light detectors and a plurality of light emitters. These additional components greatly increase the cost of the system. For example, photomultiplier tubes, which are generally quite expensive, are often used as light detector units in devices of this type. Hence, the cost of the unit is generally increased if more than one photomultiplier tube is used. However, it is desirable to use as few photomultiplier tubes as possible to maintain a competitive price for the apparatus. However, devices which employ a single detector (e.g., photomultiplier tube) are incapable of testing a plurality of samples without some type of mechanical motion for each test.

A detector apparatus is also described in U.S. Pat. No. 4,343,991, to Fujiwara et al. This apparatus employs a single light detector and a plurality of light emitting devices to read a sample on a sample carrier, which is a substantially transparent medium. In this apparatus, the plurality of light emitting devices transmit light through corresponding optical fibers. The light emitted by the optical fibers passes through the carrier and is received by corresponding optical fibers on the opposite side of the carrier. The receiving fibers terminate at a single light detector and the light emitters are operated to emit light at different times. Hence, light from only one of the emitters passes through the carrier at any given time and is detected by the detector, which outputs a signal proportional to the intensity of the detected light. Therefore, a single detector can be used to detect light from a plurality of light emitting devices. When the light passes through a portion of the carrier that includes a sample, the intensity of the light is decreased because some of the light is absorbed by the sample. The amount by which the light intensity is reduced is proportional to the concentration of the sample material in the sample. Because the signal output by the detector is proportional to the intensity of the detected light, the sample concentration can thus be determined based on the output signal.

Although the nucleic acid separating techniques, the pipetting techniques, and the sensory techniques discussed above exist separately, what is lacking, is an integrated system that synergistically combines these and other tools to create an advanced, easy-to-operate system for the isolation, amplification and detection of targeted nucleic acids to diagnose diseases by manipulating fluid samples. Past approaches to automate sample processing were limited to automating portions of the process leaving the remaining tasks to be performed by a technician. For example, many earlier systems employ a manual centrifugation step that requires a technician to load sample tubes into and out of an external centrifuge. Other systems require a technician to transfer extraction products from a nucleic acid extraction instrument to an amplification and/or detection instrument.

Certain attempts have been made at providing limited automation to sample handling systems. For example, certain systems utilize Cartesian robots for moving samples from one location to another. As known in the art, Cartesian robots can move in X, Y and Z direction, are able to perform straight-line insertions and are easy to program. Cartesian robots have the most rigid robotic structure for a given length, since the axes can be supported at both ends. Due to their rigid structure, Cartesian robots can manipulate relatively high loads. This enables them to be used for pick-and-place applications, machine tool loading, and stacking parts into bins. Cartesian robots can also be used for assembly operations and liquid dispensing systems. Examples of such uses occur in laboratory applications (genetic research), or any task that is high volume and repetitive.

One disadvantage of Cartesian robots, however, is that they require a large area of space in which to operate, or, in other words, have a large footprint to workspace ratio. Another disadvantage is that Cartesian robots have exposed mechanical elements which are difficult to seal from wet, corrosive or dusty environments, and are difficult to decontaminate.

In addition, selectively compliant articulated robot arms (SCARA) robots have been used in the genome area to pick colonies and transfer them from a media plate to a sample plate.

Although the systems discussed above may be useful in certain capacities, it a need exists to have a fully automated system for processing a component of interest, wherein such processing includes isolating, amplifying and detecting, and the component of interest includes a specific or non specific nucleic acid sequence and/or protein. Significant advantages can be realized by automating the various process steps of an assay, including greatly reducing the risk of user-error, pathogen exposure, contamination, and spillage, while increasing efficiency. Automating steps of an assay will also reduce the amount of training required for practitioners and virtually eliminate sources of injury attributable to high-volume applications.

SUMMARY OF THE INVENTION

It is therefore a general object of the invention to provide a novel processing system that will obviate or minimize problems of the type previously described.

In order to achieve this and other objects of the present invention, an automated system for processing a component of interest contained in a sample is provided comprising a sample rack, adapted for receiving at least one container containing the sample, an extraction device, adapted to extract said component of interest from the sample, a detection device, adapted to detect for the presence of said component of interest extracted by said extraction device, and a robot, adapted to automatically transfer the sample to the extraction device, and to automatically transfer said extracted component of interest from said extraction device to said detection device.

In accordance with an embodiment of the present invention, the centrifugation step discussed above is eliminated and instead accomplished with the use of a magnetic particle extractor subsystem. Utilization of non-specific nucleic acid capture provides advantages of lower reagent cost and improved robustness relative to more complex specific capture systems. The low cost of the non-specific capture particles (iron oxide) allows flexibility to increase the capture matrix and scale binding capacity without significantly impacting cost. Additionally, the system uses an industrial grade (SCARA) robotic arm that provides accurate, repeatable and reliable positioning of the pipetter as opposed to laboratory liquid handling robotic platforms that use less reliable robotic components.

BRIEF DESCRIPTION OF THE DRAWINGS

The novel features and advantages of the present invention will best be understood by reference to the detailed description of the specific embodiments which follows, when read in conjunction with the accompanying drawings, in which:

FIG. 2 illustrates a perspective view of an automated multiple specimen preparation system for the isolation, amplification and detection of targeted nucleic acid sequences in accordance with an embodiment of the invention;

FIG. 21 is a flowchart illustrating an example of steps of a method for operating the fully integrated and automated multiple specimen system for the isolation, amplification and detection of targeted nucleic acid sequences as shown in FIG. 2.

DETAILED DESCRIPTION OF THE PREFERRED EMBODIMENT

Figure 1:
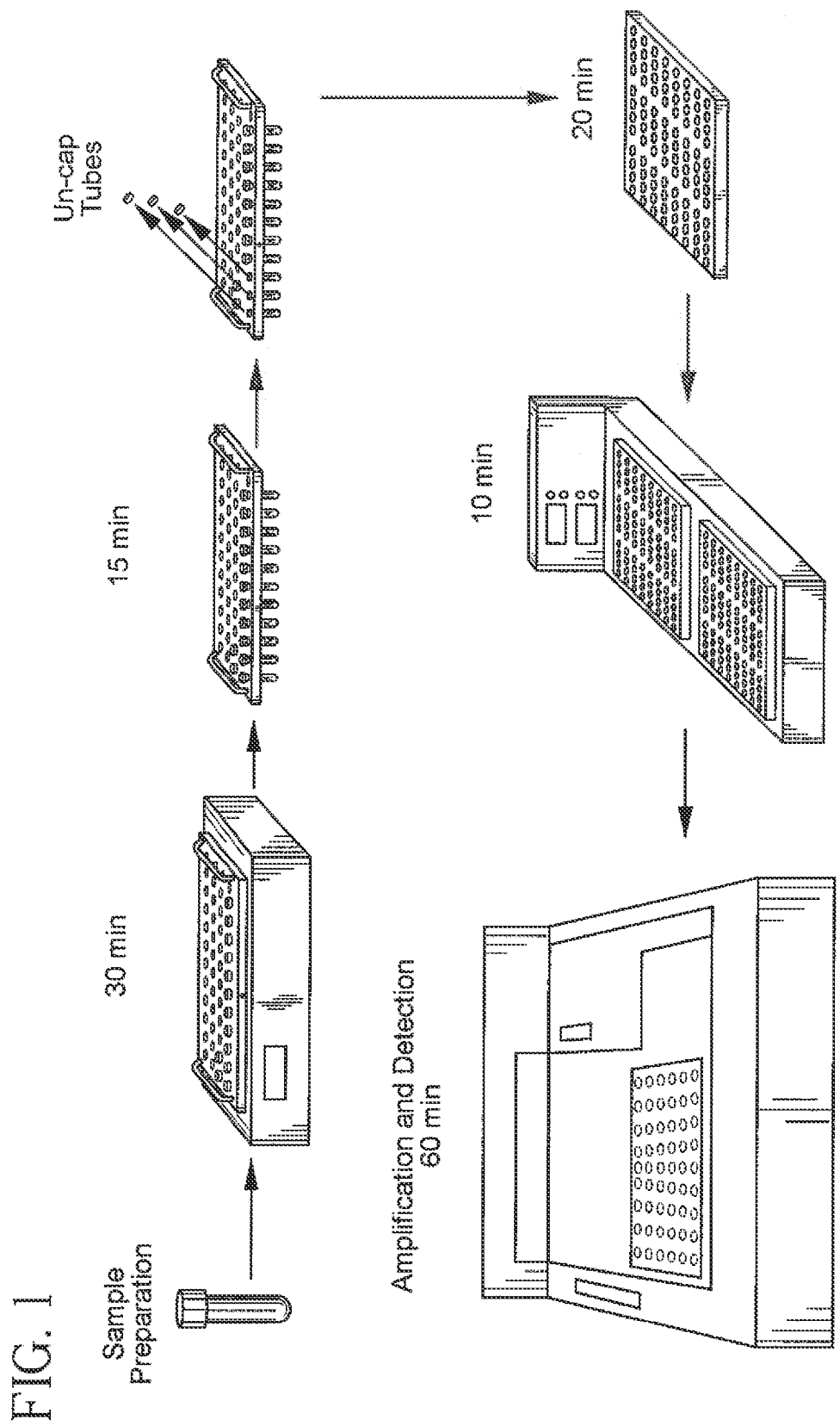
FIG. 1 illustrates a known method for manually preparing multiple specimen samples for the isolation, amplification and detection of targeted nucleic acid sequences.

The various features of the preferred embodiment will now be described with reference to the figures, in which like parts are identified with the same reference characters.

FIG. 1 illustrates a known method for manually preparing multiple specimen samples for the isolation, amplification and detection of targeted nucleic acid sequences which employs the BDProbeTec™ ET System that provides sensitive and specific detection of Chlamydia trachomatis (CT) and Neisseria gonorrhoeae (GC) from clinical samples. The technology is based on homogeneous Strand Displacement Amplification (SDA) and detection of target DNA. Currently, samples are processed, lysed and manually pipetted from sample tubes to priming and amplification wells. The system 200, illustrated in FIG. 2 (and discussed in detail below) has been developed to minimize pipetting and reduce hands-on time associated with the BDProbeTec™ ET CT/GC assays by automating pipetting from sample tubes to extractor, isolating the component of interest and then transferring the component of interest to priming wells and from priming to amplification wells.

As discussed in more detail below, the system 200 achieves reliable automation through the use of an industrial grade robotic arm 524 (see FIGS. 3 and 5) which in this embodiment is a selectively compliant articulated robot arm (SCARA) that has a mean time between failure of 20,000 hours or 10 years of single shift use. The pipetter assembly 522 is comprised of pipetter tips 528, as well as other components, which have a range of 20-1100 µL+/−10% with >1 year Preventative Maintenance Interval (PMI) or 1,000,000 cycles. Unlike other clinical instrumentation, the system 200 utilizes no perishable tubing for fluid movement.

Procedure for Setting Up the System 200

First, power is turned on in the system 200. Second, pipette tips are loaded on to the system 200. Third, the priming and amplification microwells are loaded onto the system 200. Then, in step four, samples are loaded onto an instrument deck. Sample parameters and assay type are chosen via a touch screen in step five, and in step 6 the system 200 is enabled to run the processing program.

The system 200 minimizes hands-on pipetting while achieving the same CT/GC specimen results per shift as the BDProbeTec™ ET manual system.

Figure 3:
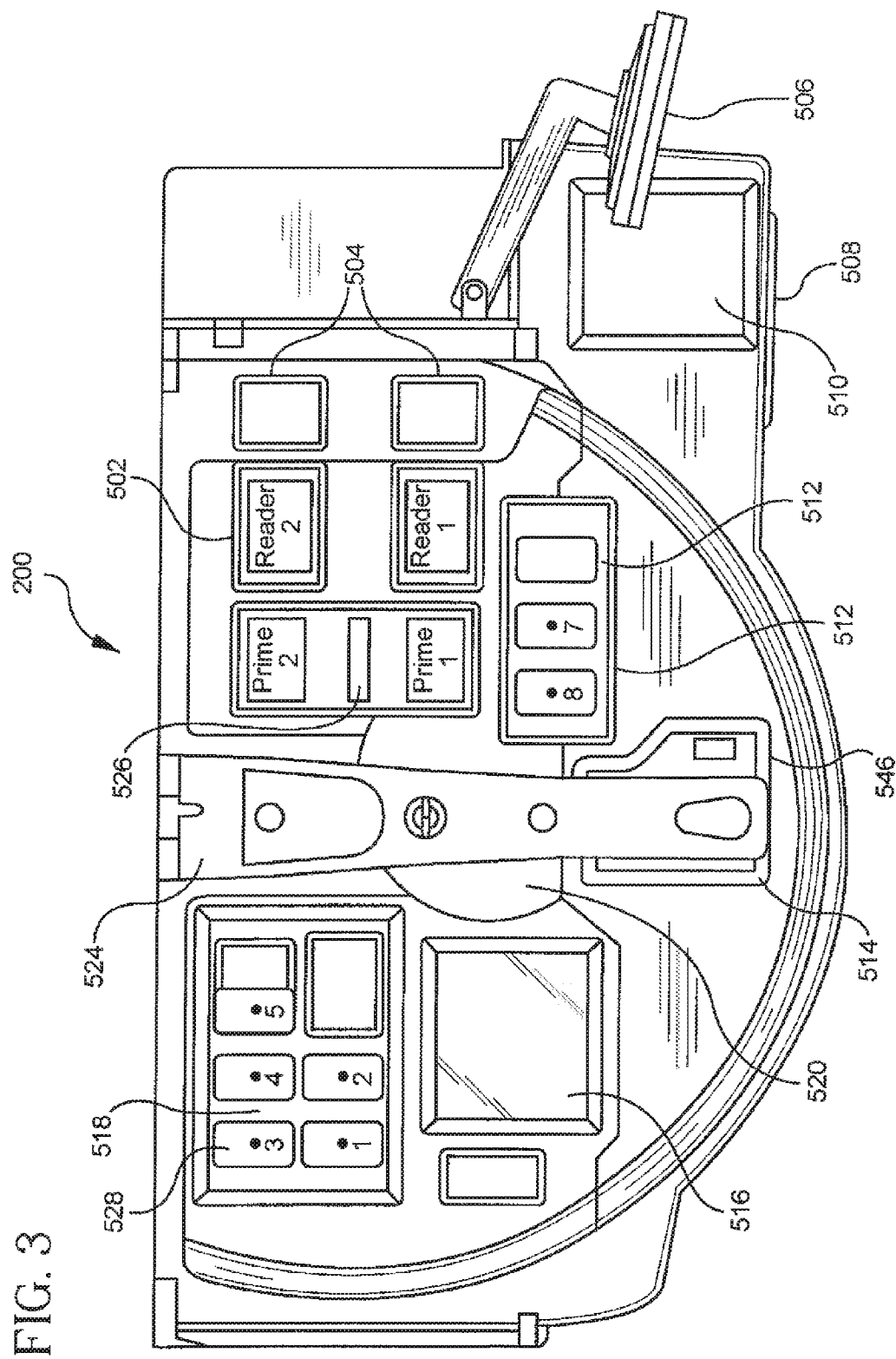
FIG. 3 illustrates an internal view of the fully integrated and automated multiple specimen system for the isolation, amplification and detection of targeted nucleic acid sequences as shown in FIG. 2 in accordance with an embodiment of the invention.

As will now be described, the system 200 shown in FIG. 2 can be used for the isolation, amplification and detection of components of interest in accordance with an embodiment of the invention. These components of interest can include the specific or non specific capture of nucleic acids and/or proteins. FIG. 3 illustrates a block diagram of a fully integrated and automated multiple specimen system for the isolation, amplification and detection of targeted nucleic acid sequences in accordance with an embodiment of the invention. The automated multiple specimen preparation system (system) 200 shown in FIG. 3, is comprised of an assay reader stage 502, plate seals 504, LCD touch screen 506, keyboard drawer 508, tube rack with identification system (tube ID rack) 510, pipette tip holder 512, input sample tube rack 514, extractor 516, 5 position tip rack reagent trough 518, waster port 520, robotic arm 524 and priming heater plates 526 (with vacuum tool).

There exists more than one type of extraction device that can be used in accordance with the embodiments of the invention, more fully described below, as one skilled in the art can appreciate. One such extraction device is extractor 516, which is described in detail in U.S. patent application Ser. No. 09/573,540 "System and Method for Manipulating Magnetic Particles in Fluid Samples to Collect DNA or RNA from a Sample," T. Hansen et al., and U.S. patent application Ser. No. 09/858,889 "System and Method for Manipulating Magnetic Particles in Fluid Samples to Collect DNA or RNA from a Sample," T. Hansen et al. Additionally, the pipetter assembly 522 is more fully described in U.S. patent application Ser. No. 10/073,207 "A System and Method for Verifying the Integrity of the Condition and Operation of a Pipetter Device For Manipulating Fluid Samples," T. Hansen et al.

There exists more than one type of detection device that can be used in accordance with the embodiments of the invention, more fully described below, as one skilled in the art can appreciate. One such detection device is the assay reader 502 more fully described in U.S. Pat. No. 6,043,880 "Automated Optical Reader for Nucleic Acid Assays", J. Andrews et al. these and other types of detection devices were described briefly in the background of the invention. The contents of each of the above referenced U.S. patent applications and U.S. patents are expressly incorporated herein by reference.

Figure 4:
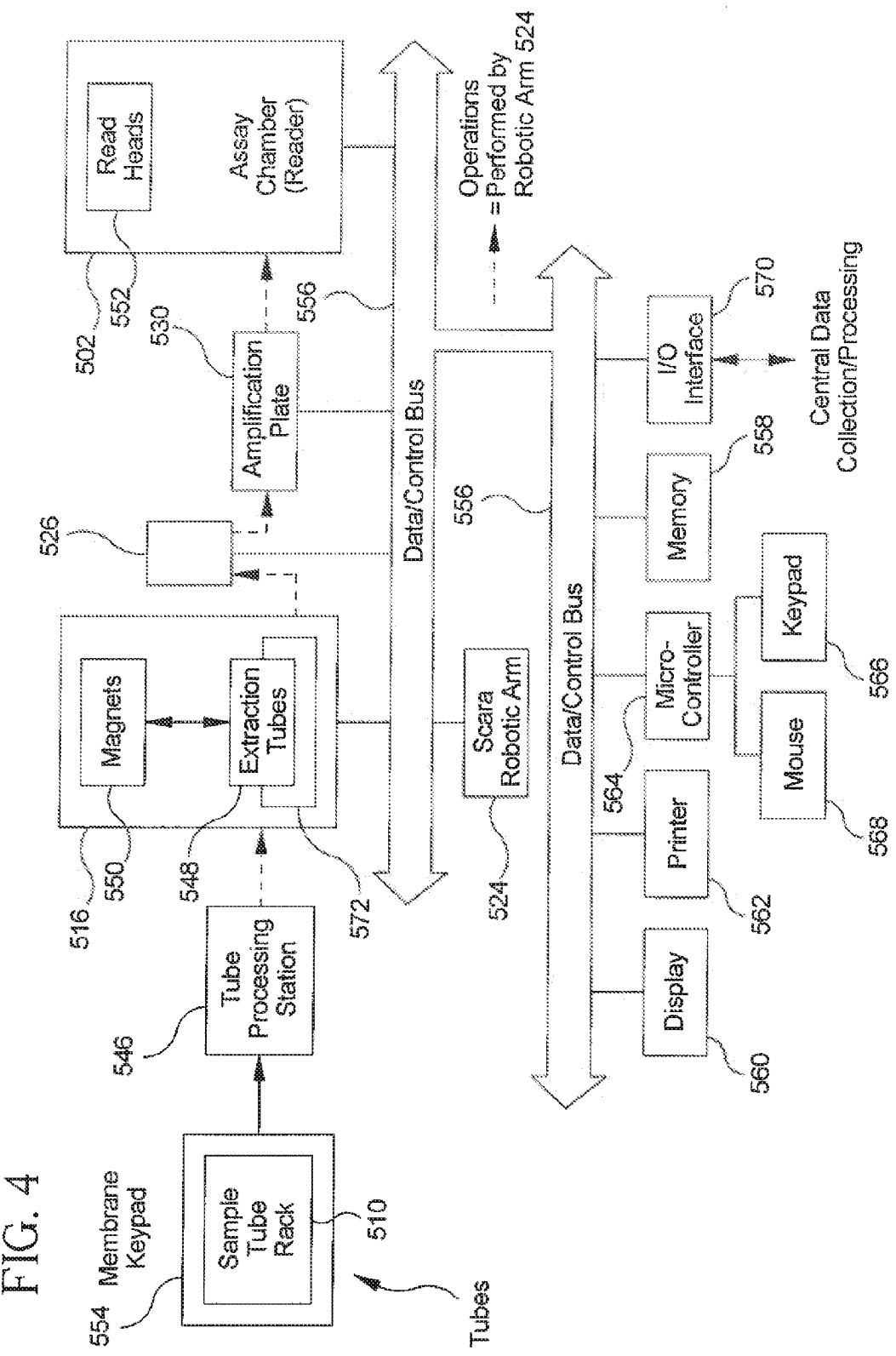
FIG. 4 illustrates a system block diagram of the major components of a fully integrated and automated multiple specimen system as shown in FIG. 2 and more fully described in reference to FIG. 3 and related figures.

FIG. 4 illustrates a conceptual block diagram at the system 200, showing the main components of the system 200, and how samples are processed. The dashed lines illustrate when robotic arm 524 is used to move sample material (with pipette tips 528) and other devices. FIG. 4 includes a micro-controller (which can also be a "local" or "remote" PC) 564, or any other suitable controller. Throughout the following discussion, and especially in conjunction with the accompanying description of the method illustrated in FIG. 21, operation of system 200 is controlled by a program which can be stored and operated locally and/or remotely. A detailed description of such devices and method of operation is excluded, as one skilled in the relevant and related arts can understand its operation. Such a controller can include a display 560, printer 562, micro-controller 564, with mouse 568 and/or keypad 566, memory 558, I/O interface 570 and data/control bus 556.

Figure 9:
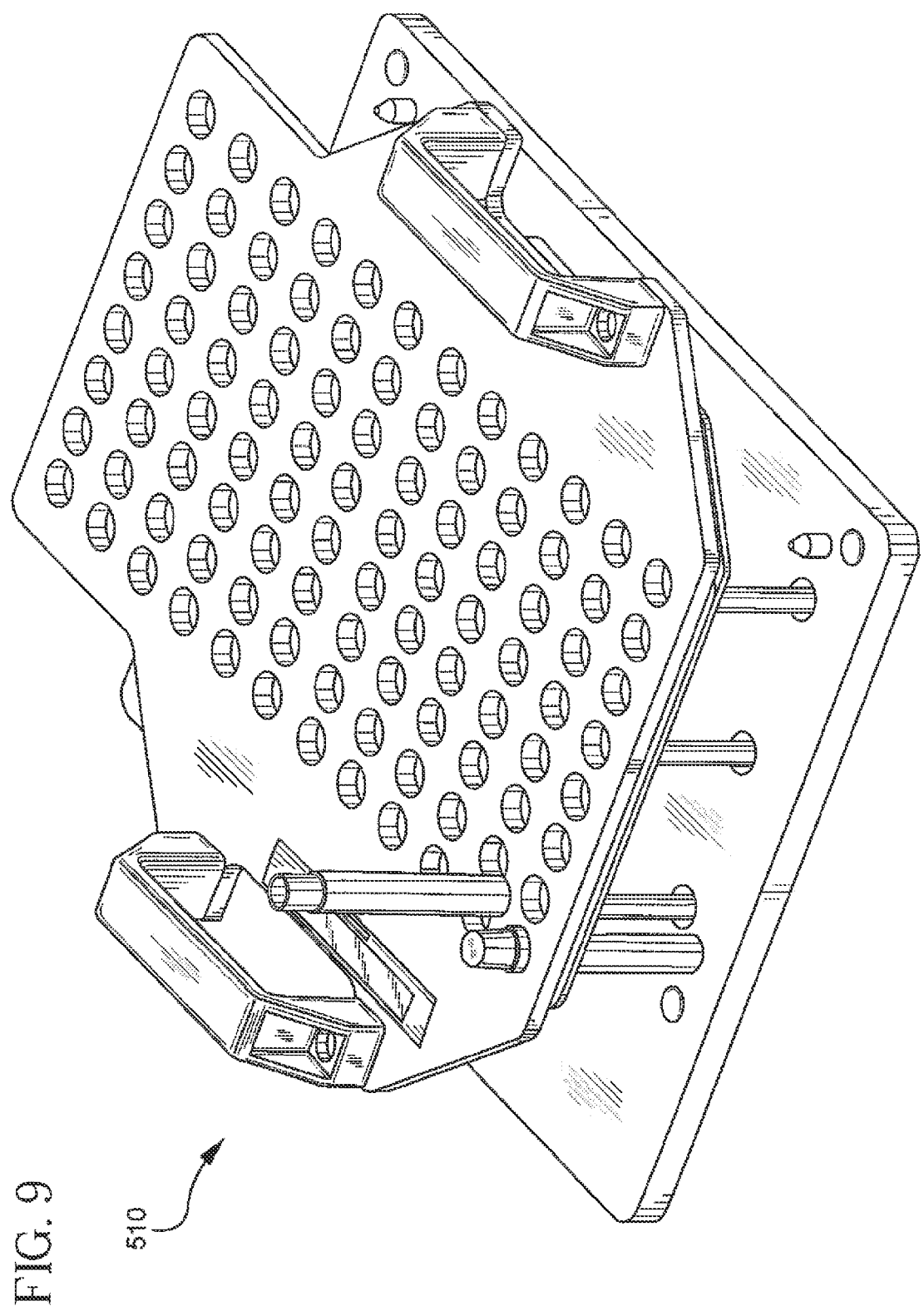
FIG. 9 illustrates a perspective view of a tube rack with an identification system for use in the integrated and automated multiple specimen system for the isolation, amplification and detection of targeted nucleic acid sequences as shown in FIGS. 2 and 3 in accordance with an embodiment of the invention.
Figure 10:
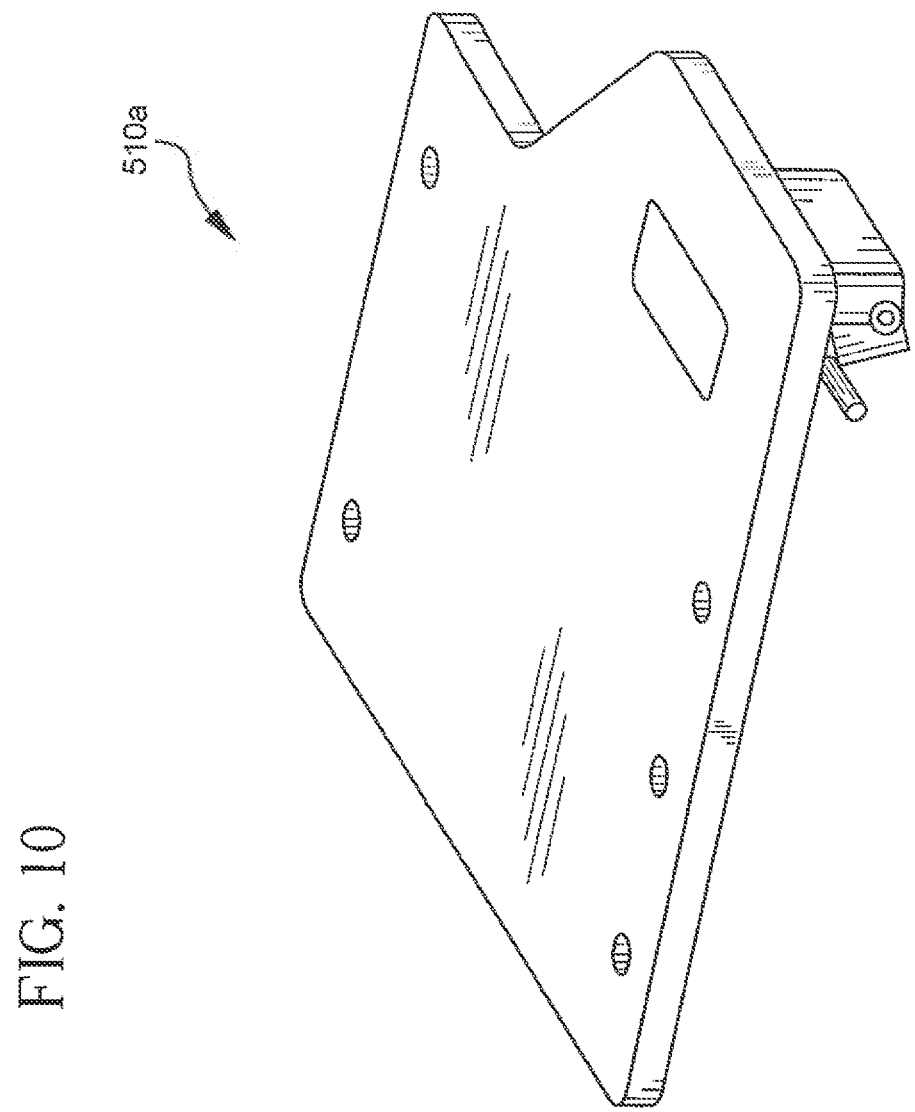
FIG. 10 illustrates a perspective of a portion of the tube rack identification station as shown in FIG. 9 for use in the integrated and automated multiple specimen system for the isolation, amplification and detection of targeted nucleic acid sequences in accordance with an embodiment of the invention.
Figure 11:
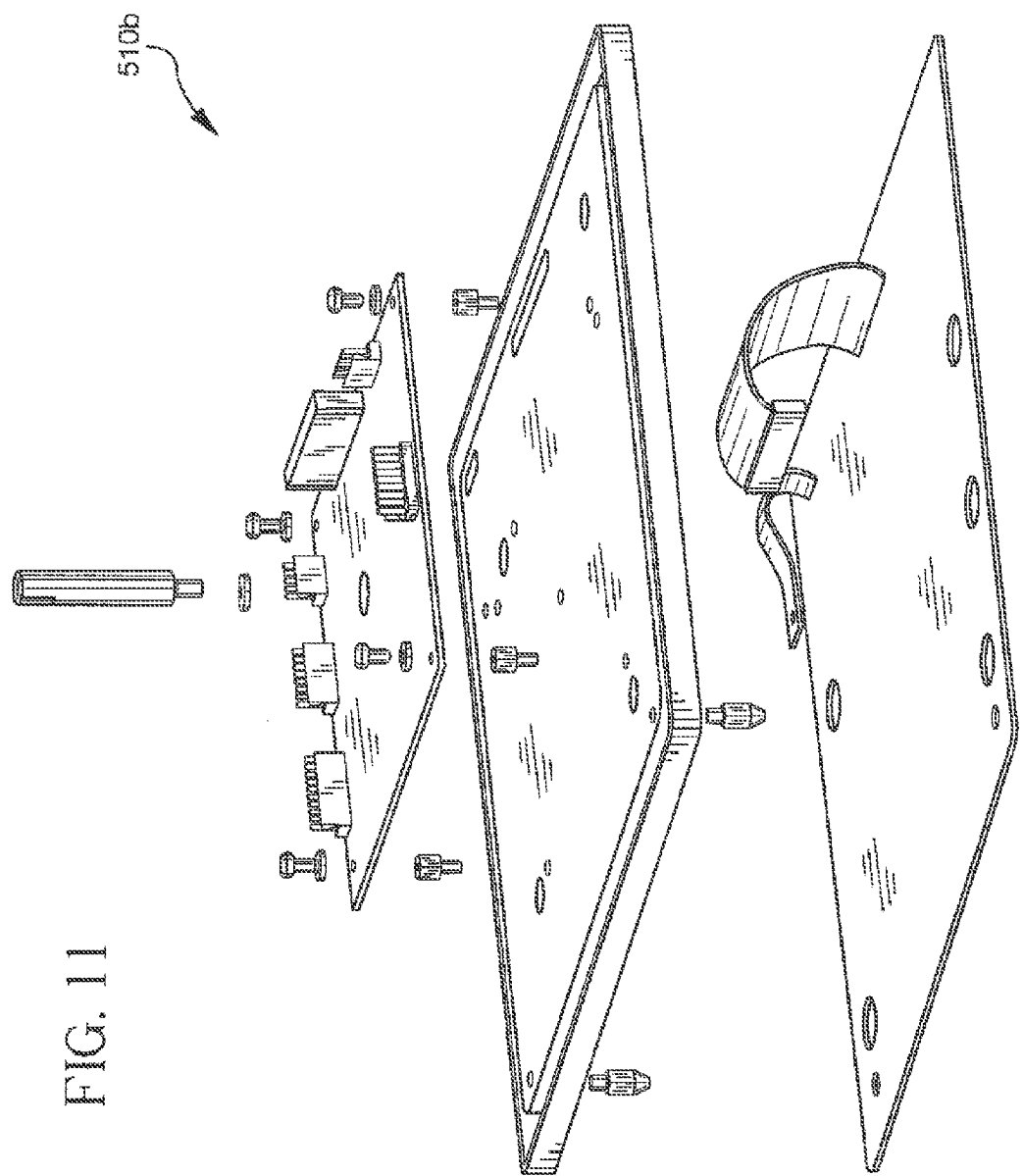
FIG. 11 illustrates an exploded perspective view showing a portion of the tube rack identification station assembly as shown in FIG. 9 for use in the integrated and automated multiple specimen system as shown in FIGS. 2 and 3 for the isolation, amplification and detection of targeted nucleic acid sequences in accordance with an embodiment of the invention.
Figure 12:
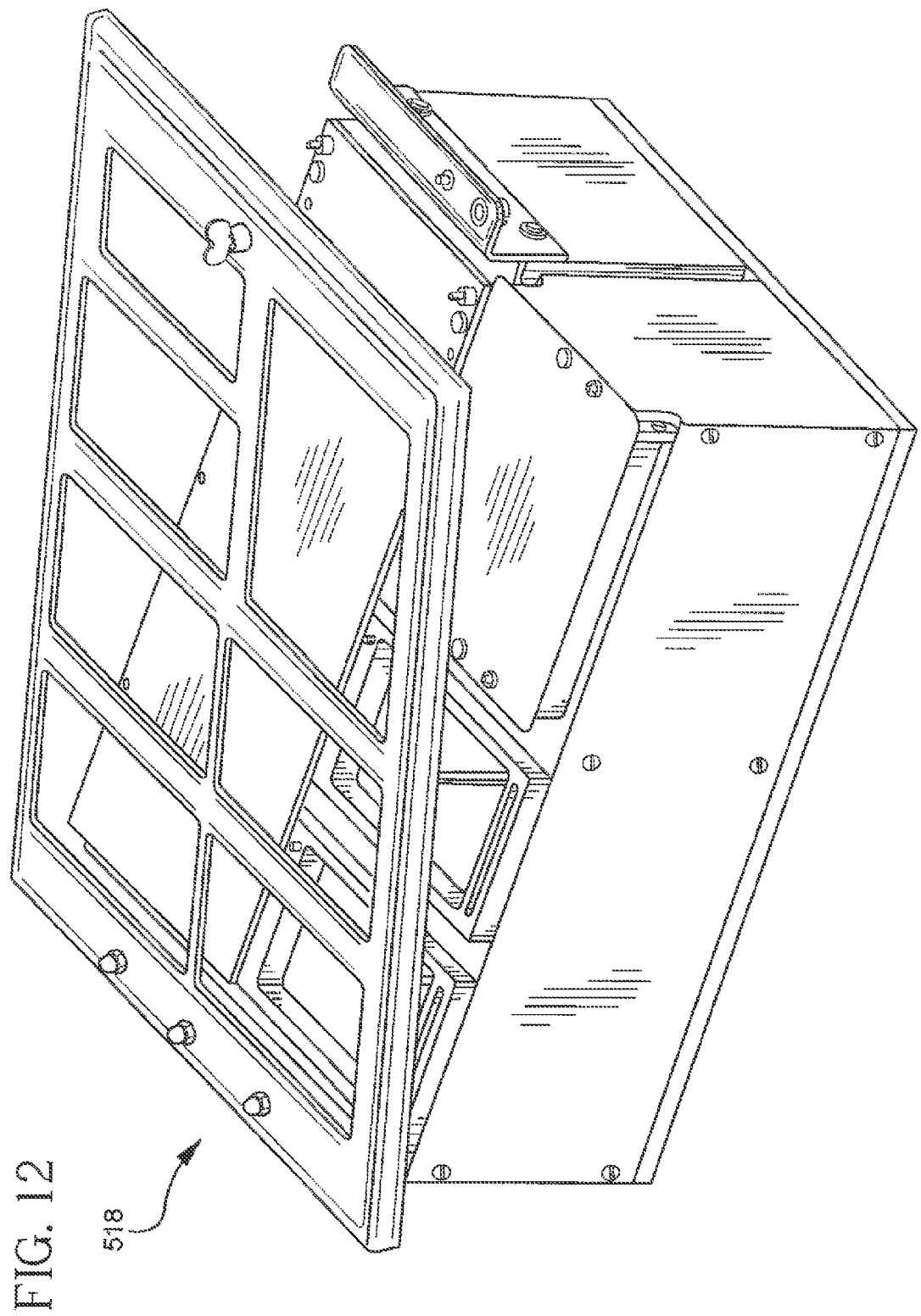
FIG. 12 illustrates a perspective view of a pipette tip holder station for use in the integrated and automated multiple specimen system for the isolation, amplification and detection of targeted nucleic acid sequences as shown in FIGS. 2 and 3 in accordance with an embodiment of the invention.
Figure 13:
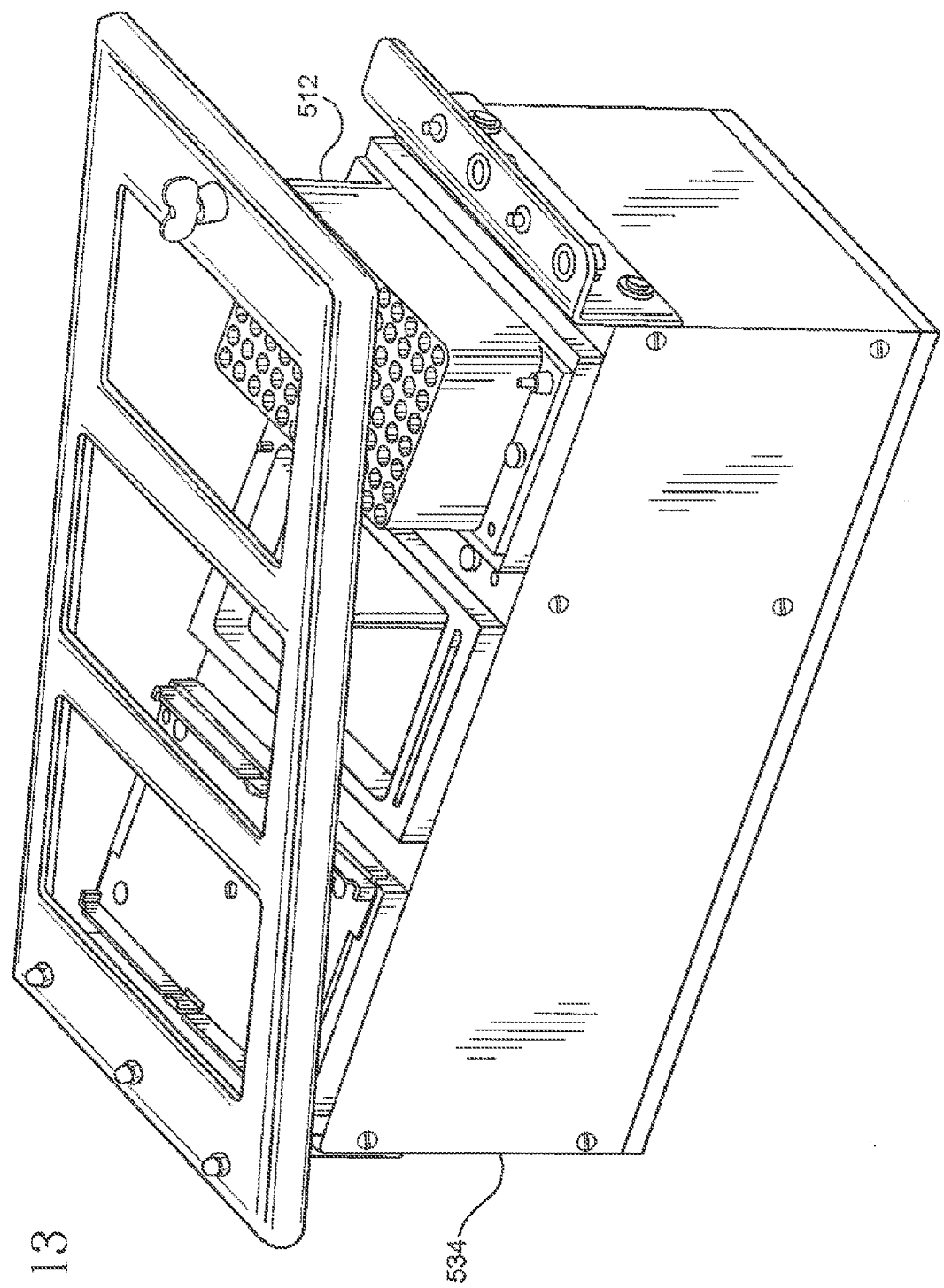
FIG. 13 illustrates a perspective view of a pipetter tip holder with tip exchange station for use in the integrated and automated multiple specimen system for the isolation, amplification and detection of targeted nucleic acid sequences as shown in FIGS. 2 and 3 in accordance with an embodiment of the invention.
Figure 14:
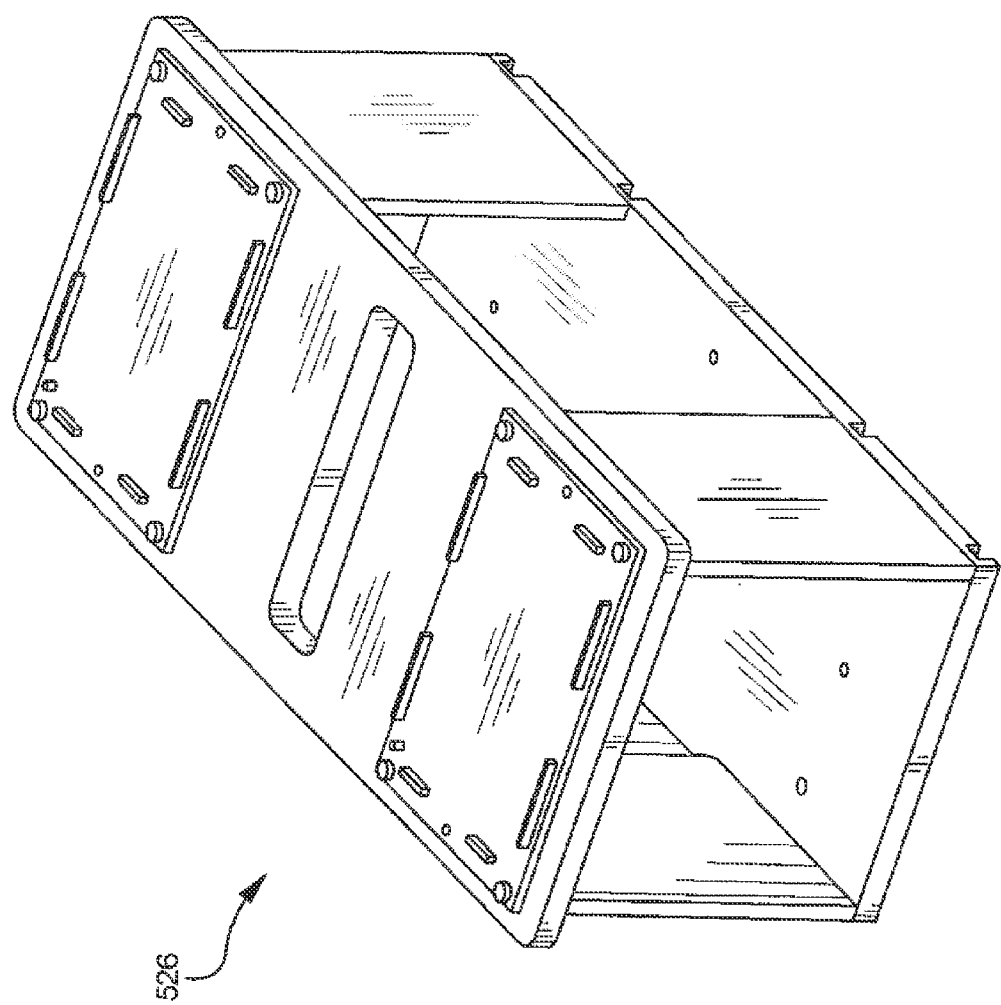
FIG. 14 illustrates a perspective view of priming heater plates for use in the integrated and automated multiple specimen system for the isolation, amplification and detection of targeted nucleic acid sequences as shown in FIGS. 2 and 3 in accordance with an embodiment of the invention.
Figure 15:
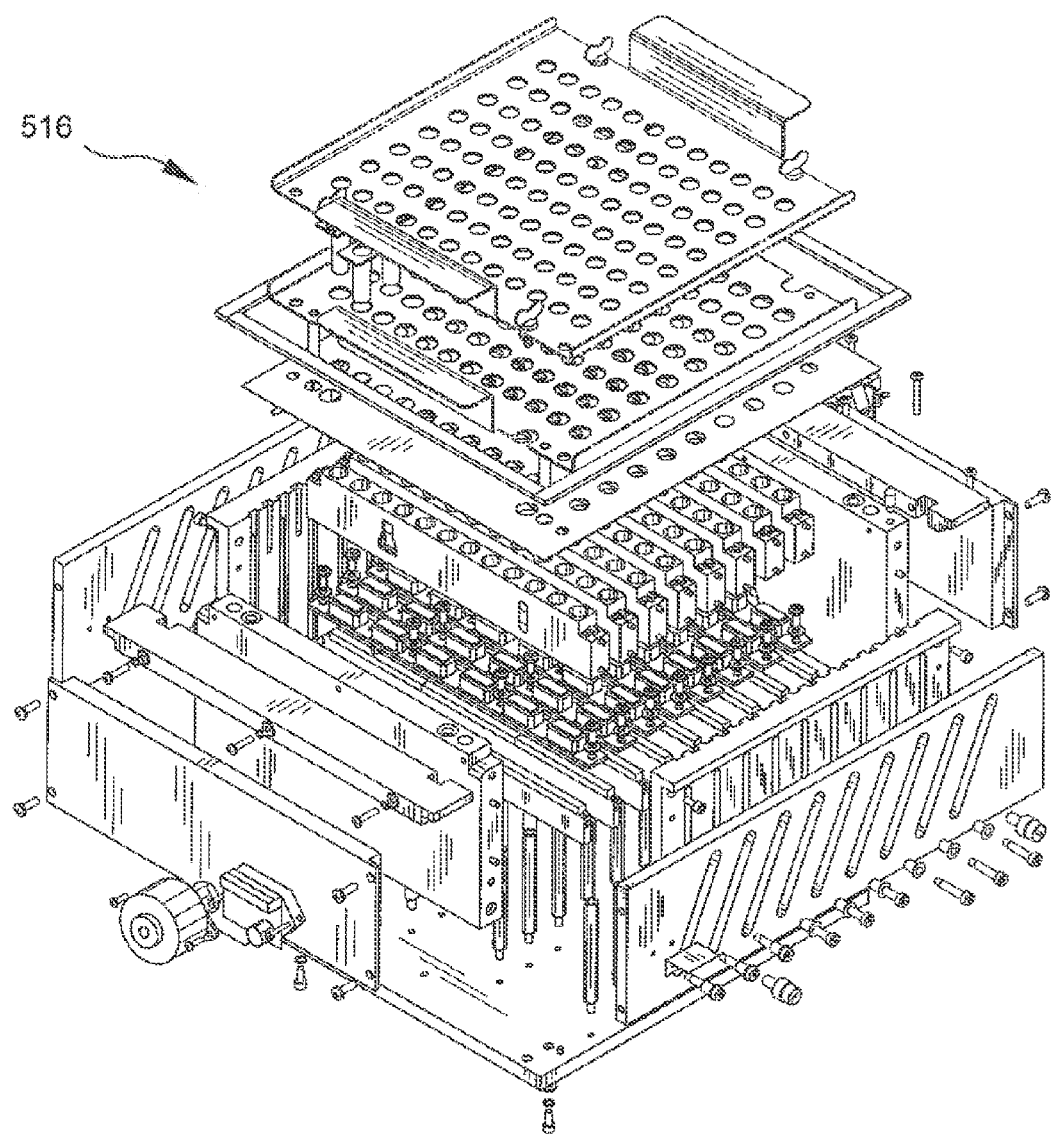
FIG. 15 illustrates an exploded perspective view of an extractor system for use in the integrated and automated multiple specimen system for the isolation, amplification and detection of targeted nucleic acid sequences as shown in FIGS. 2 and 3 in accordance with an embodiment of the invention.
Figure 16:
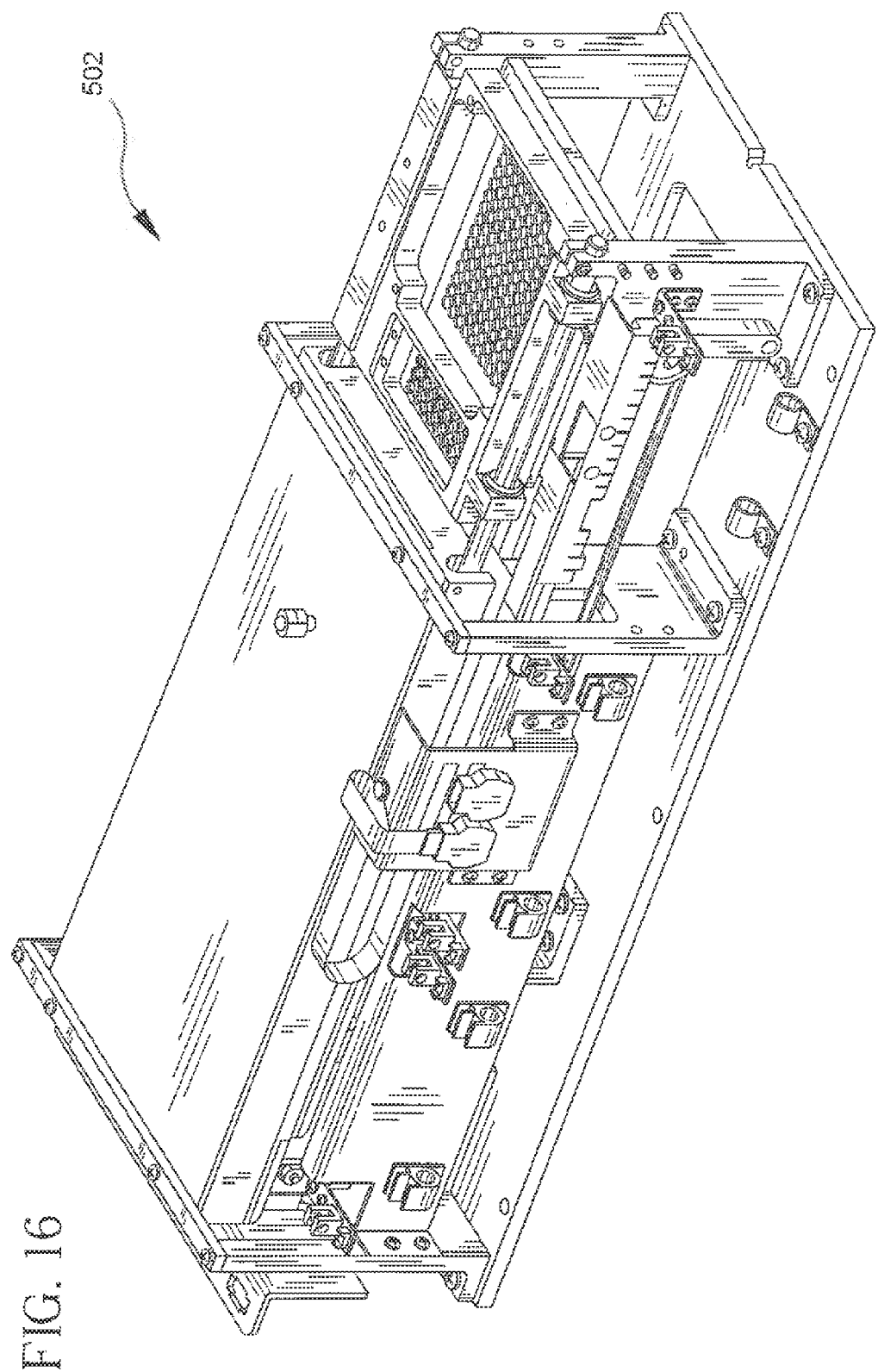
FIG. 16 illustrates a perspective view of an assay reader stage for use in the integrated and automated multiple specimen system for the isolation, amplification and detection of targeted nucleic acid sequences as shown in FIGS. 2 and 3 in accordance with an embodiment of the invention.
Figure 17:
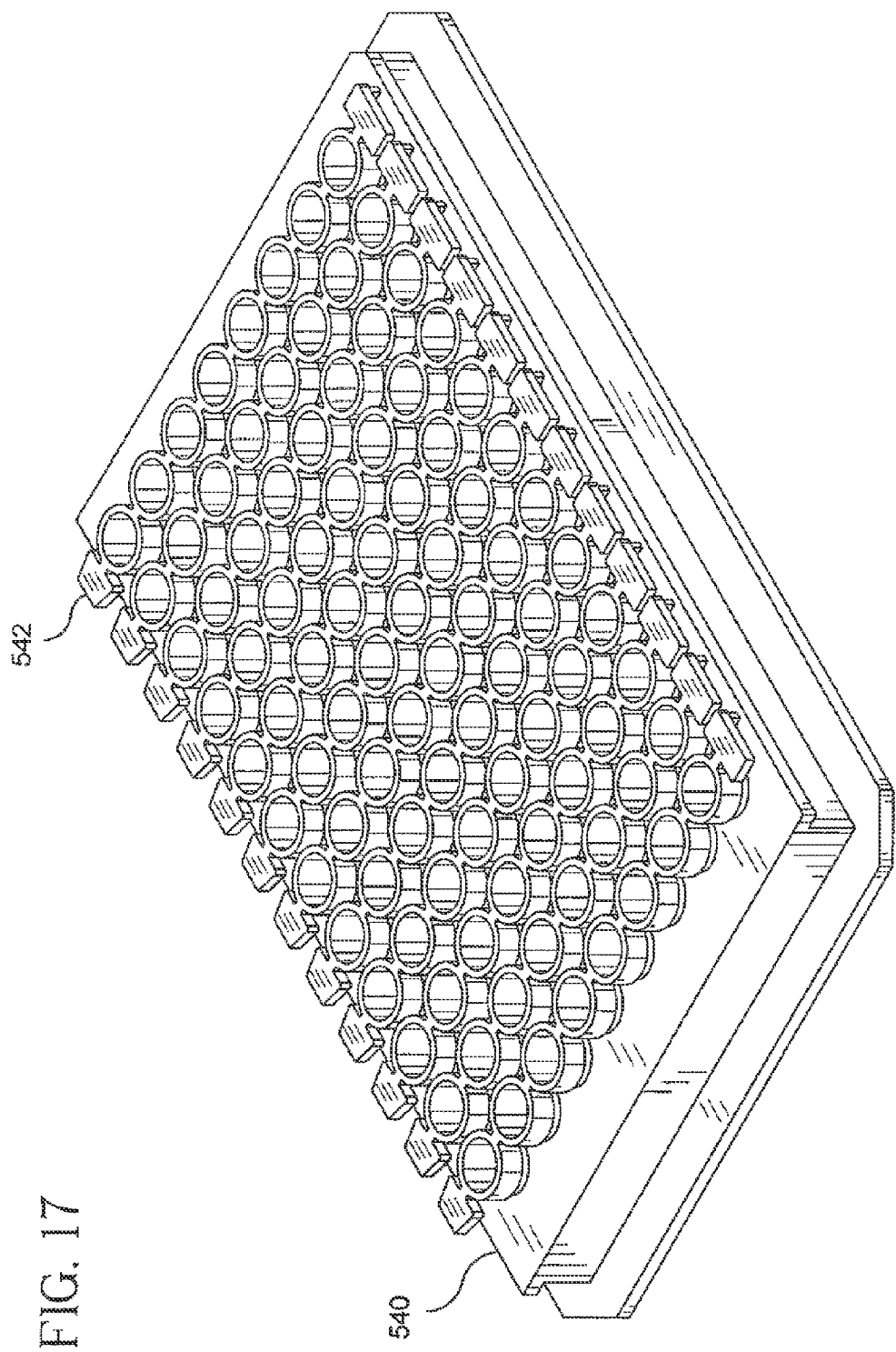
FIG. 17 illustrates a perspective view of multiple position microtiter plate with wells for use in the assay ready of FIG. 16 in the integrated and automated multiple specimen system for the isolation, amplification and detection of targeted nucleic acid sequences as shown in FIGS. 2 and 3 in accordance with an embodiment of the invention.
Figure 18:
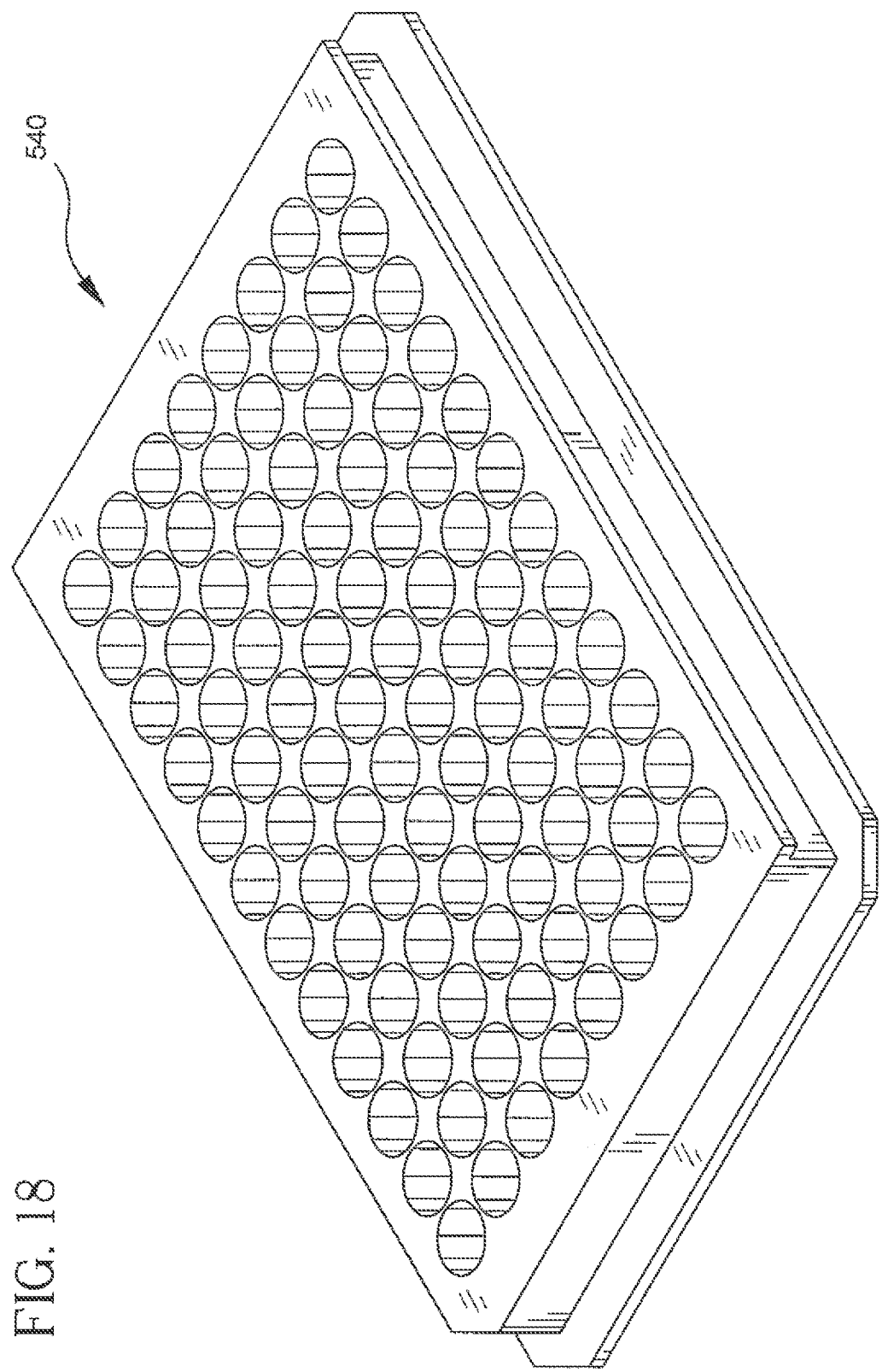
FIG. 18 illustrates a perspective view of a multiple position microtiter plate as shown in FIG. 17.
Figure 19:
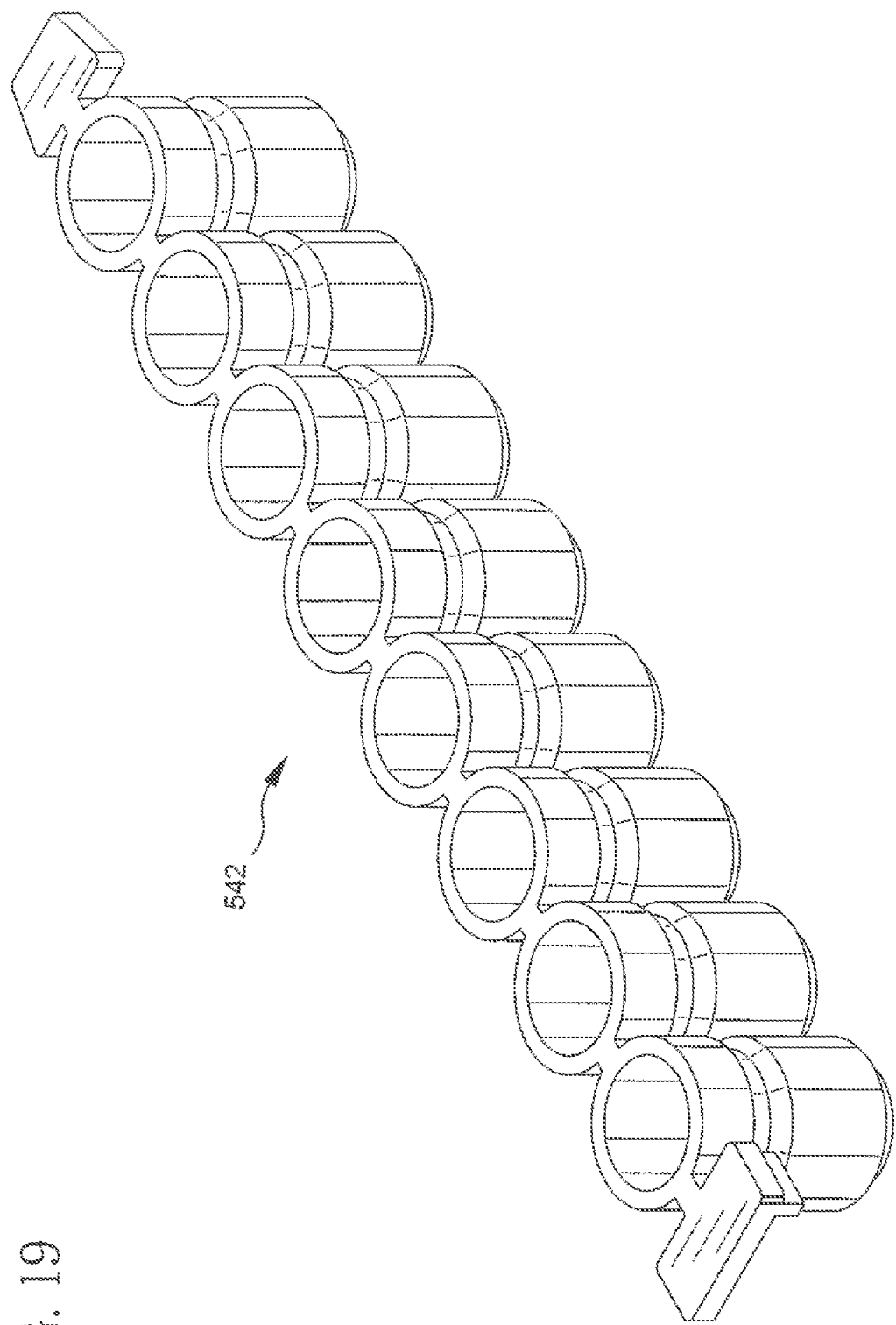
FIG. 19 illustrates a perspective view of a portion of a microtiter well assembly as shown in FIG. 17.
Figure 20:
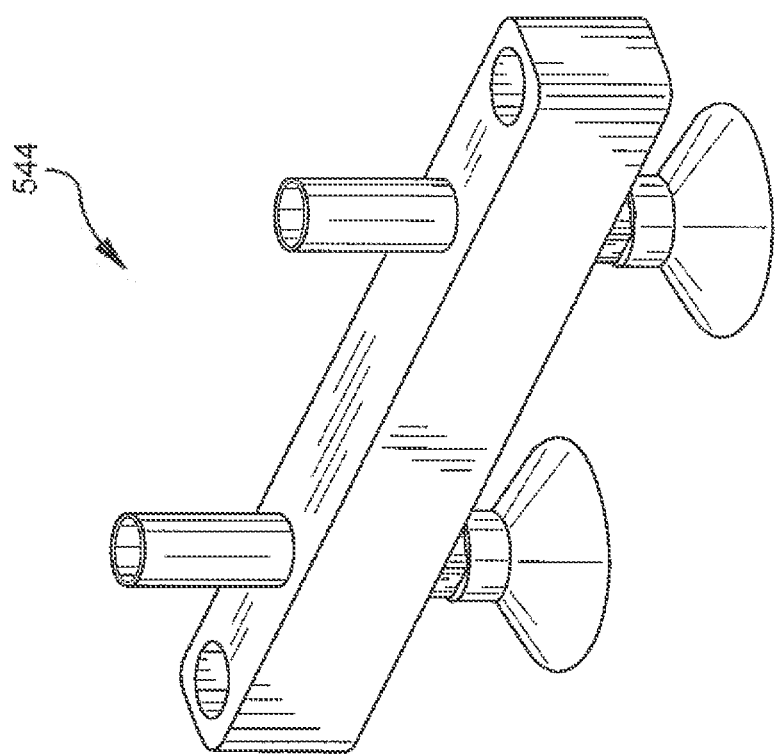
FIG. 20 illustrates a perspective view of a plate sealer gripper tool for use in applying a sealing plate to the microtiter plate shown in FIG. 17 in the integrated and automated multiple specimen system for the isolation, amplification and detection of targeted nucleic acid sequences as shown in FIGS. 2 and 3 in accordance with an embodiment of the invention.

As discussed above, the automated system 200 makes use of a robotic arm 524 to perform all the steps required to isolate and amplify nucleic acid from a fluid sample. Components include an input sample tube rack 510 with sample tacking mechanism (FIGS. 9-11), an extractor subsystem used to isolate and concentrate nucleic acid from input sample (FIG. 15), heated priming and amplification stations (FIG. 14) used for the amplification of isolated nucleic acid and readers which monitor amplification of specific target analytes (FIG. 16). All steps of the process are fully automated by the use of an industrial grade robotic arm (FIG. 5) with an attached pipetting apparatus (FIGS. 6-8, 12 and 13) capable of transferring fluids using disposable pipette tips 528 to prevent cross contamination of liquid samples. The pipetting assembly 522 makes use of pressure transducers to detect the presence of filtered pipette tips 528 on the nozzle of the pipetter and to sense liquid levels in sample test tubes (FIGS. 9-11). A computer program that allows run-specific input to be entered via an integrated LCD touch screen monitor 506 controls all processing steps.

The system 200 is fully self-contained in an enclosure with sliding acrylic windows that protects the operator from the moving robotic arm 524 and prevents any aerosols that may be present in the liquid samples from escaping. Replaceable containers, accessible from below the instrument are used to collect the contaminated pipette tips 528 and liquid waste.

Operation of the system 200 employing the SCARA robotic arm 524 will now be discussed as can be appreciated by one skilled in the art, a SCARA robot has motions very much like a human body. These devices incorporate both a shoulder and elbow joint as well as a wrist axis and a vertical motion. SCARA robots were invented in Japan in the early 1960's and have been used extensively in many different industries since then.

Figure 5:
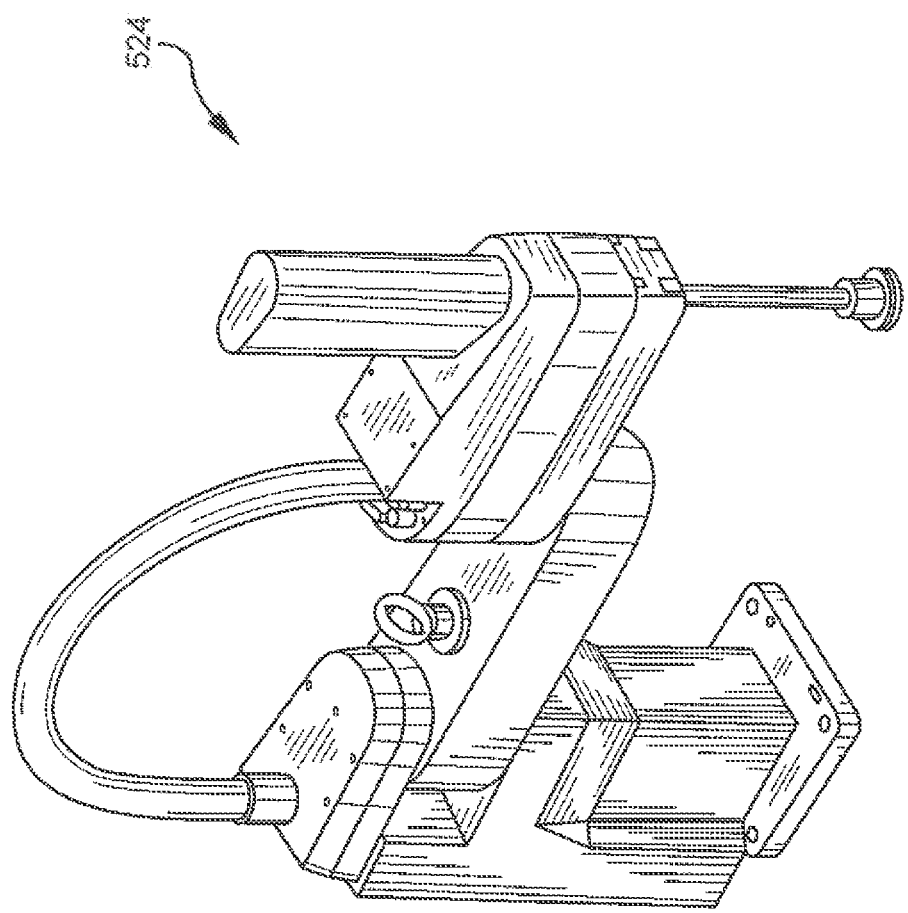
FIG. 5 illustrates a perspective view of a SCARA robotic arm used in the integrated and automated multiple specimen system for the isolation, amplification and detection of targeted nucleic acid sequences in accordance with an embodiment of the invention.
Figure 6:
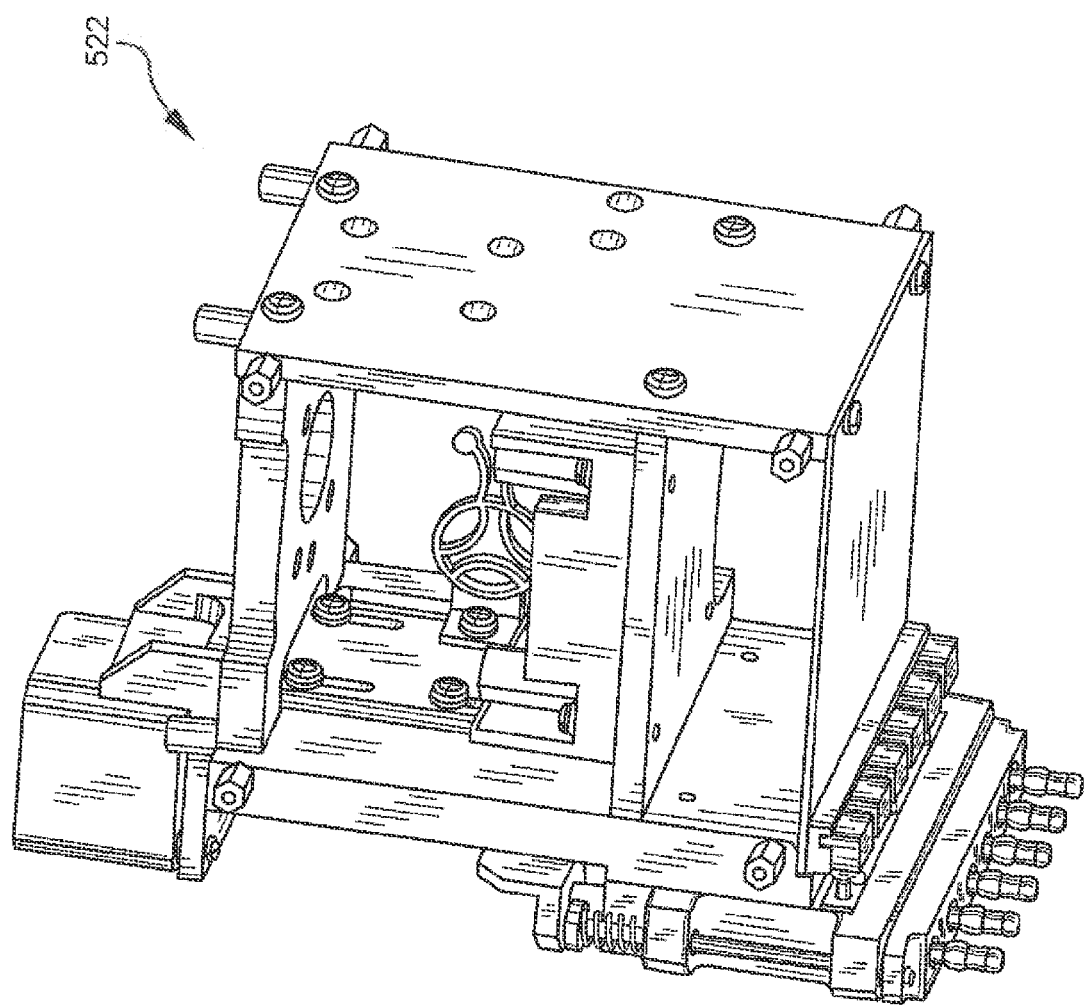
FIGS. 6 and 7 illustrate different perspective views of a six channel pipetter assembly used in the integrated and automated multiple specimen system shown in FIG. 2 for the isolation, amplification and detection of targeted nucleic acid sequences in accordance with an embodiment of the invention.
Figure 7:
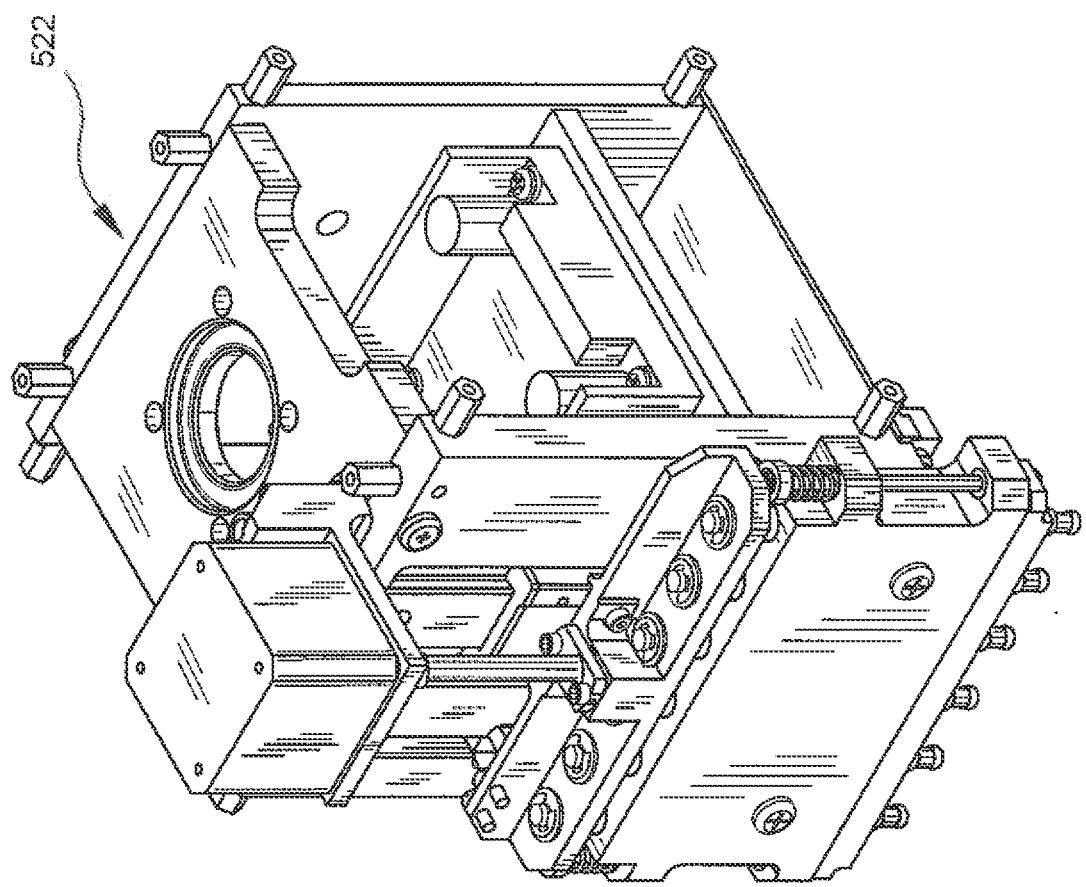
Figure 8:
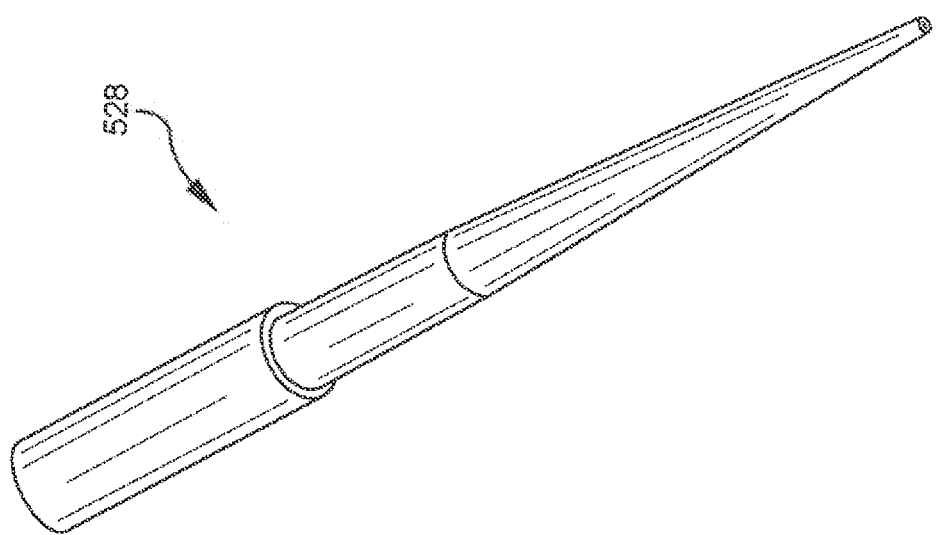
FIG. 8 illustrates an example of a pipetter tip used with the pipetter assembly shown in FIGS. 6 and 7 in the integrated and automated multiple specimen system shown in FIG. 2 for the isolation, amplification and detection of targeted nucleic acid sequences in accordance with an embodiment of the invention.

SCARA robots are ideal for a variety of general purpose applications which require fast, repeatable, and articulate, point-to-point movements. Examples of their uses include palletizing & de-palletizing, loading and unloading, and assembly. Because of their unique "elbow" motions, SCARA robots are also ideal for applications which require constant acceleration through circular motions, such as dispensing and gasket-forming in-place. SCARA robot joints are all capable of rotation and can be thoroughly sealed and safeguarded, which is necessary should the robot be deployed in dusty or corrosive environments. SCARA robots are generally faster than Cartesian robots and can perform multiple motions at their joints. Robotic arm 524, illustrated in FIG. 5, is an example of a SCARA-type robotic arm. It should be also noted that the system 200 is not limited to the use of a SCARA, but rather can use any other suitable type of robotic device, such as an articulated robot, that will enable the system 200 to perform its intended functions.

The following is a description of the method described in FIG. 21, in which reference is made to a specific use of one of the embodiments of the invention, which is the processing of a targeted nucleic acid. However, as has been described above, and as one skilled in the art can appreciate, the invention is not limited to this specific embodiment, nor to the processing of a targeted nucleic acid, but the invention has several different embodiments, and can instead be used for the processing of targeted or non-targeted nucleic acids and/or targeted or non-targeted proteins. Referring to FIG. 21, the method for operating the system 200, begins with step 102, in which the user first loads the disposable pipette tips 528, extractor tubes, liquid reagents, priming and amplification microwells and plate seals. Next, an empty sample tube rack 510 is placed into the tube rack log in station. The operator scans the tube rack bar 510 code via the handheld bar code wand and then scans each sample tube to be tested and places the tube into the tube rack 510. As each tube is placed into the tube rack 510, a membrane keypad 554 mounted below the tube rack 510 is activated, communicating the location of the tube to the computer. The operator continues to wand each tube and places it into the tube rack 510 until all tubes to be processed are loaded. At the end of this process the computer has logged the tube rack 510 identity and the patient information and location of each tube loaded in the tube rack 510.

The tube rack 510 is then placed into the tube processing station 546. A stationary bar code reader located below the tube rack 510 reads the tube rack 510 identification and relates the tube rack 510 identification to the database of patient information logged for that particular tube rack 510. This information is tracked to the final stage of the process when the patient results are printed. Next the user closes the acrylic windows and initiates the run via the LCD touch screen 506.

In step 104, robotic arm 524 picks-up pipette tips 528 and transfers fluid from each sample tube into a corresponding extraction tube 548. The extraction tubes are pre-filled with magnetic particles and lysing reagents and covered with a foil film that the robotic arm 524 punctures when dispensing the fluid sample into the tube. The robotic arm 524 mixes the sample to resuspend the extraction tube components. All mixing steps can be conducted, but not necessarily, under the influence of a degaussing field to facilitate particle dispersion. The robotic arm 524 disposes of the pipette tips 528 and acquires new pipette tips 528 after each sample transfer. This process continues until all of the samples have been transferred into their corresponding extractor tubes. Alternatively, the sample may be loaded directly into the extractor device. In this embodiment the sample is in a container which may be pre-filled with the necessary reagents and/or material for extraction.

During the next step, step 106, heaters 572 within the extractor subsystem 516 heat the sample to a suitable temperature that causes the release of nucleic acid from the microorganisms contained in the biological sample. The heaters 572 are then disabled allowing the lysed samples to cool. Alternatively, instead of using heat, or in combination with heat, the nucleic acid may be released from the microorganisms contained in the biological sample by chemical means. Means of chemical extraction are described in "Chemical Pre-treatment of Plasma for Nucleic Acid Amplification Assays," U.S. Ser. No. 10/359,180 and "Pretreatment Method for Extraction of Nucleic Acid from Biological Samples and Kits Therefor", U.S. Ser. No. 10/359,179.

After cool down, the robotic arm 524, in step 108, picks up new pipette tips 528, aspirates binding reagent, dispenses and mixes binding reagent into the first group of extraction tubes using a different pipette tip 528 for each sample. This process non-specifically binds the nucleic acid onto the magnetic particles. Next, in step 110, magnets 550 within the extractor subsystem 516 are automatically moved into position to collect the magnetic particles to the sides of the tubes. The robotic arm 524, using the same pipette tips 528, aspirates the waste liquid from each extractor tube leaving the magnetic particles with attached total nucleic acid locked to the side of the tube (step 111). The magnets 550 are then moved to their original position below the tubes, thus releasing the particles from the sides of the tubes.

In step 112 robotic arm 524 picks up new pipette tips 528, aspirates the wash reagent, dispenses, and then mixes the wash reagent with the magnetic particles and bound nucleic acid material. In step 114 the magnets 550 are then moved into position to lock the particles to the sides of the tube and the robotic arm 524, using the same pipette tips 528 removes the liquid waste wash reagent (step 115), leaving the washed, nucleic acid bound particles locked to the side of the tubes. The magnets 550 are then moved to the position below the tubes. In step 116 elution buffer is aspirated into pipette tips 528. The elution buffer is then dispensed into, and mixed with, the magnetic particles, thereby releasing the total nucleic acid from the magnetic particles (step 117). A volume of elution buffer which is lower relative to the input sample volume can be utilized to effectively concentrate the nucleic acids. In step 118 the magnets 550 are moved up to the lock-down position and the robotic arm 524 pipettes the eluted sample containing concentrated nucleic acid into the priming wells (step 119). Further details of the non-specific nucleic acid binding processes are set forth in U.S. patent application Ser. No. 09/858,889, referenced above.

After a 20 minute room temperature incubation period, the priming heater plates 526 are enabled, elevating the temperature of the priming wells to a suitable heat spike temperature, which disrupts non-specifically hybridized oligonucleotides (step 120). In step 121, robotic arm 524 then aspirates the appropriate volume of sample from the priming wells and dispenses it into the amplification/reader wells. After all of the samples have been transferred from the priming heater plate 526 to the amplification plate 530, the robotic arm 524 picks-up the plate seal gripper tool 544, picks-up a plate seal 504 and places the plate seal 504 on the amplification plate 530. The sealed amplification plate 530 is transferred into the assay reader chamber 502, which maintains as series of temperatures required for amplification of target nucleic acids (step 122).

In step 124, the assay reader chamber 502 moves the sealed amplification plate 530 over the read heads 552 to detect nucleic acid amplification products. The assay reader chamber 502 determines the test result, and provides the data via a printout. The locations of the test results match the location of the original sample tubes. Two sets of priming plates and two sets of amplification/reader plates are provided to support one or two tests per sample. Further details of the assay reader are set forth in U.S. Pat. No. 6,043,880, referenced above.

Alternative methods of sample processing include automating nucleic acid extraction with the use of silica membranes. In this case, lysed sample fluids mixed with binding reagents are pipetted into an open vessel with a silica membrane suspended in the center. A vacuum is employed to draw the sample through the membrane trapping the nucleic acid in the membrane and allowing the remaining waste fluid to be discarded. Reagents are then used to release the nucleic acid from the membrane. Issues with automating this approach require the assembly and disassembly of a vacuum chamber. Using automation to achieve this complex task can be problematic especially since all parts must be airtight. Additionally, unused sections of the device must be blocked (usually manually with tape) to allow an even vacuum to be achieved over the active portion of the device.

Efficient capture of total nucleic acids (including low copies of specific targets of interest) is particularly challenging in the more viscous, high-protein samples such as plasma. Through optimization of the extraction process, we have developed protocols utilizing the system 200, which allow efficient capture of nucleic acids in viscous samples such as plasma and expressed vaginal swabs. Key advances included minimizing protein pre-coating of particles by introducing the particles after plasma treatment. This reduces competition for potential binding sites between protein and nucleic acids and reduces aggregation of particles due to protein-protein interactions. Minimization of particle aggregation, in turn, facilitates more efficient particle mixing. The implementation of a degaussing field during aspiration mixing also enhances mixing efficiency by minimizing particle aggregation due to residual particle magnetism. The combination of these advances allows efficient nucleic acid extraction from viscous, proteinaceous samples without the aid of chaotropic salts.

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

The invention claimed is:

1. A method for processing a component of interest contained in a sample, comprising:
   receiving at least one tube containing a sample in a sample rack;
   automatically transferring the sample from the tube to an extraction device comprising a tube using a selectively compliant articulated robot arm (SCARA);
   operating the extraction device to extract said component of interest from the sample while the sample is disposed in the extraction device tube;
   automatically transferring the extracted component of interest from the extraction tube in the extraction device to a primer well and from a primer well to an amplification/reader well disposed in an amplification plate, wherein the automatically transferring includes operating the SCARA to perform said transferring;
   automatically picking up a plate seal gripper tool and sealing the amplification plate using the SCARA;
   moving the amplification plate to a detector wherein the amplification plate is moved using the SCARA; and
   operating a detector to detect for the presence of said component of interest extracted by said extraction device.

2. A method as claimed in claim 1, wherein:
   the component of interest includes a nucleic acid;
   the extraction device operating step extracts the nucleic acid from the sample; and
   the detection device operating step detects the presence of the extracted nucleic acid.

3. A method as claimed in claim 1, wherein:
   the extracted component of interest includes a nucleic acid; and
   the detection device operating step includes amplifying the nucleic acid.

4. A method as claimed in claim 3, wherein:
   the amplifying includes heating the nucleic acid.

5. A method as claimed in claim 1, wherein:
   the extraction device operating step performs non-specific capture of the component of interest to extract the component of interest from the sample.

6. The method as claimed in claim 5, wherein the component of interest is a nucleic acid.

7. The method as claimed in claim 5, wherein the component of interest is a protein.

8. The method as claimed in claim 1, wherein the extraction device and detection device are integrated as a single unit.

9. The method as claimed in claim 1, further comprising:
   receiving at least one container containing the sample in a sample rack.

10. A method for automatically extracting nucleic acid from a sample, comprising:
    operating a selectively compliant articulated robot arm (SCARA);
    extracting the nucleic acid from the sample with an extractor comprising a tube configured to receive the sample from a sample tube, wherein operating said SCARA comprises moving the sample from the sample tube to the extractor tube using a first pipette tip retrieved by the SCARA;
    transferring the extracted nucleic acid from the extractor tube to a well in an amplification plate using the SCARA, wherein a second pipette tip retrieved by the SCARA is used for the transfer;
    sealing the amplification plate using the SCARA wherein the SCARA picks up a plate seal and places the plate seal on the amplification plate;
    and
    transferring the amplification plate into a detector device using the SCARA.

11. A method for automatically extracting a target nucleic acid from a sample, comprising:
    operating an extractor comprising a tube to perform non-specific capture on the target nucleic acid to extract the nucleic acid from the sample without separating the target nucleic acid from non-target nucleic acid that may exist in the sample;

operating an amplifier to amplify the extracted nucleic acid; and automatically transferring the extracted nucleic acid from the extractor tube to sample wells in an amplifier plate;

automatically sealing the amplifier plate;

automatically transferring the amplifier plate to a detector, where the automatically transferring steps and the automatically sealing step all use a selectively compliant articulated robot arm (SCARA) to perform the steps.

12. A method as claimed in claim 11, further comprising:
automatically transferring the sample from a container to said extractor tube.

13. A method as claimed in claim 11, further comprising:
automatically transferring fluid to the extractor to assist the extractor in extracting the target nucleic acid.

14. An automated process for isolating and amplifying a target nucleic acid sequence that may be present in a sample, said process comprising:

automatically separating the target sequence from the fluid sample at a separation station by performing non-specific binding on the target sequence without the need to physically separate the target sequence from any non-target sequence that may exist in the sample prior to separating;

automatically transporting the separated target sequence from the separation station to an amplifying incubation station using a selectively compliant articulated robot arm (SCARA);

automatically picking up a plate seal gripper tool and sealing the amplification plate using the SCARA; and automatically transporting an amplification plate having wells containing the separated target sequence from the amplifying incubation station to a detection station using the SCARA.

* * * * *